(12) United States Patent
Tajima

(10) Patent No.: US 6,509,193 B1
(45) Date of Patent: Jan. 21, 2003

(54) METHOD AND APPARATUS FOR CONTROLLING MAGNETIC PARTICLES BY PIPETTING MACHINE

(75) Inventor: Hideji Tajima, Inagi (JP)

(73) Assignee: Precision System Science Co., Ltd., Tokyo (JP)

( * ) Notice: Subject to any disclaimer, the term of this patent is extended or adjusted under 35 U.S.C. 154(b) by 0 days.

(21) Appl. No.: 09/197,408

(22) PCT Filed: May 20, 1996

(86) PCT No.: PCT/JP96/01333

§ 371 (c)(1),
(2), (4) Date: Apr. 16, 1999

(87) PCT Pub. No.: WO97/44671

PCT Pub. Date: Nov. 27, 1997

(51) Int. Cl.[7] .................. G01N 35/10; G01N 33/543; B01L 3/02
(52) U.S. Cl. ................. 436/49; 210/222; 210/695; 422/63; 422/100; 422/101; 436/43; 436/54; 436/174; 436/179; 436/180; 436/807; 702/19
(58) Field of Search ............ 436/43, 47, 49, 436/54, 174, 177, 180, 807, 809, 810; 422/63–67, 100, 101; 210/695, 222, 223; 702/19

(56) References Cited

U.S. PATENT DOCUMENTS

| | | | | |
|---|---|---|---|---|
| 4,785,677 A | * | 11/1988 | Higo | 73/864.14 |
| 5,158,895 A | * | 10/1992 | Ashihara et al. | 136/526 |
| 5,183,638 A | * | 2/1993 | Wakatake | 422/64 |
| 5,289,385 A | * | 2/1994 | Grandone | 364/497 |
| 5,576,215 A | * | 11/1996 | Burns et al. | 436/50 |
| 5,646,049 A | * | 7/1997 | Tayi | 436/518 |
| 5,647,994 A | * | 7/1997 | Tuunanen et al. | 210/695 |
| 5,702,950 A | * | 12/1997 | Tajima | 436/49 |

FOREIGN PATENT DOCUMENTS

EP  0410645  * 5/1991

* cited by examiner

*Primary Examiner*—Arlen Soderquist
(74) *Attorney, Agent, or Firm*—Haynes and Boone, LLP

(57) ABSTRACT

The present invention relates to a method and apparatus for controlling magnetic particles by a sample distributor and is intended to process a sample liquid with high precision, sensitivity and reliability by arresting magnetic particles to separate them from the liquid and by suspending the magnetic particles in a liquid to mix the magnetic particles with the liquid again.

The pipette portion of this invention has a front end portion, a reservoir portion, a liquid passage connecting the front end portion and the reservoir portion, and a separation region in the liquid passage that is subjected to a magnetic field. The pipette portion of this construction draws in or discharges a liquid for processing. This invention includes a process in which when a magnetic particle-suspended liquid is passed through the separation region of the pipette portion, a magnetic field is applied to the separation region from outside the liquid passage to attract the magnetic particles to the inner surface of the liquid passage, thereby separating the magnetic particles from the liquid.

66 Claims, 20 Drawing Sheets

[Assay parameter maintenance]

STEP Name

Protocol No.

Protocol name  [C company (Y) 2nd pattern]

41d            41e
                     A:0083  C:0089   SA:0076
                     B:0101  D:0000   SB:0094
                              T:0373   SC:0182

| HOLE | 1 | 2 | 3 | 4 | 5 | 6 | 7 | 8 | 9 | 10 |
|---|---|---|---|---|---|---|---|---|---|---|
| STEP | Fe | Cl.- | Co | Cl.- | Su.- | Co-- | --- | --- | --- | --- |
| Reagent 1 (μl) | 100 | 300 | 200 | 300 | 200 | 50 | 0 | 0 | 0 | 0 |
| Reagent 2 (μl) | 0 | 0 | 0 | 0 | 0 | 0 | 0 | 0 | 0 | 0 |
| Sample (μl) | 100 | 0 | 0 | 0 | 0 | 0 | 0 | 0 | 0 | 0 |
| Number of agitations | 5 | 4 | 4 | 4 | 4 | 0 | 0 | 0 | 0 | 0 |
| Agitation before arresting | 0 | 0 | 0 | 0 | 0 | 0 | 0 | 0 | 0 | 0 |
| INC second | 373 | 0 | 373 | 0 | 0 | 100 | 0 | 0 | 0 | 0 |
| Arresting, yes 1 or no 0 | 1 | 0 | 0 | 0 | 0 | 0 | 0 | 0 | 0 | 0 |
| Sample SEQ | 3 | 5 | 7 | 9 | 0 | 0 | 0 | 0 | 0 | 0 |
| Arresting SEQ | 2 | 4 | 6 | 8 | 10 | 0 | 0 | 0 | 0 | 0 |
| Agitation SEQ | 0 | 0 | 0 | 0 | 11 | 0 | 0 | 0 | 0 | 12 |

Trigger liquid distribution Y/N 100 (μl)

41b, 41c

METHOD AND APPARATUS FOR CONTROLLING MAGNETIC PARTICLES BY PIPETTING MACHINE

This application is a National Stage Application of PCT/JP96/01333, filed May 20, 1996.

BACKGROUND OF THE INVENTION

1. Field of the Invention

The present invention relates to a magnetic particle control method and apparatus using a sample distributor, which separates magnetic particles combined with a target substance from a liquid by magnetic force or suspends them in a liquid.

2. Description of Related Art

In recent years, a method has come to be used in a biotechnology field, which separates only a target substance from a liquid by using magnetic particles. This method has found a wide range of applications such as immunoassay, DNA hybridization, PCR, separation of cells, separation or washing of protein.

Separation of an objective substance by using magnetic particles has conventionally been achieved in the following manner. A piston in a syringe-like cylinder is manually lifted to draw a liquid containing magnetic particles into the cylinder. During this suction process, the magnetic particles in the liquid are attracted to magnets arranged on the outer side of the cylinder or of a container of the distribution tip portion (liquid reservoir portion). Then, the piston is lowered to discharge the liquid, leaving the magnetic particles adhering to the inner surface of the distribution tip portion. In this way, the magnetic particles are separated.

Then, with the magnetic particles separated from the liquid, the piston is raised again to draw another liquid into the tip thereby resetting the magnetic action on the magnetic particles. As a result, the magnetic particles are suspended in the liquid. In this condition, the piston is lowered to discharge the magnetic article-suspended liquid from the tip.

With such a manual separation or suspension method, it is practically impossible to enhance precision and sensitivity of the processes, such as attaching and detaching the pipette tip, putting the magnets toward and away from the pipette tip, controlling the relative positions of the pipette tip and the magnets, and separation, agitation and cleaning of magnetic particles. Hence, a highly automated sample distribution system is essential for controlling the magnetic particles systematically with high precision.

SUMMARY OF THE INVENTION

To perform a highly sensitive control by applying a magnetic field to the magnetic particles requires a complex and delicate setting of magnetic field, cylinder shape and operating conditions.

The present invention has been accomplished under these circumstances.

A primary objective of the present invention is to provide a control method and apparatus for controlling magnetic particles by an improved sample distributor.

A second objective of this invention is to provide a control method and apparatus for controlling magnetic particles by a sample distributor, in which not only separation and movement but also agitation, cleaning, re-suspending and mixing of magnetic particles are made possible with a highly automated sample distributor by performing a variety of liquid suction and discharge operations according to various settings and their combinations, such as speed, quantity and number of repetitions, to realize reliable control in highly precise amounts of liquids.

A third objective is to provide a control method and apparatus for controlling magnetic particles by a sample distributor, which applies a magnetic field to magnetic particles highly responsively to enable precise and complex control.

A fourth objective is to provide a control method and apparatus for controlling magnetic particles by a sample distributor, which enables complex and reliable control by simple operations.

A fifth objective is to provide a control method and apparatus for controlling magnetic particles by a sample distributor, which can automatically set and specify the most efficient and fast processing.

A sixth objective is to provide a control method and apparatus for controlling magnetic particles by a sample distributor, which can perform safe, uncontaminated, reliable processing.

A seventh objective is to provide a control method and apparatus for controlling magnetic particles by a sample distributor, which can be realized with a simple and inexpensive construction.

An eighth objective is to provide a control method and apparatus for controlling magnetic particles by a sample distributor, which can specify a variety of operations by setting various processing patterns and is therefore versatile and applicable to a wide range of applications

BRIEF DESCRIPTION OF DRAWINGS

FIG. 11 is an example page on the display screen in the first embodiment showing items to be processed that can be specified;

FIGS. 17a–7c is a schematic view showing a configuration of the apparatus as the fourth embodiment of this invention;

DESCRIPTION OF THE PREFERRED EMBODIMENTS

Now, preferred embodiments of this invention will be described in detail by referring to the accompanying drawings.

Figure 1:
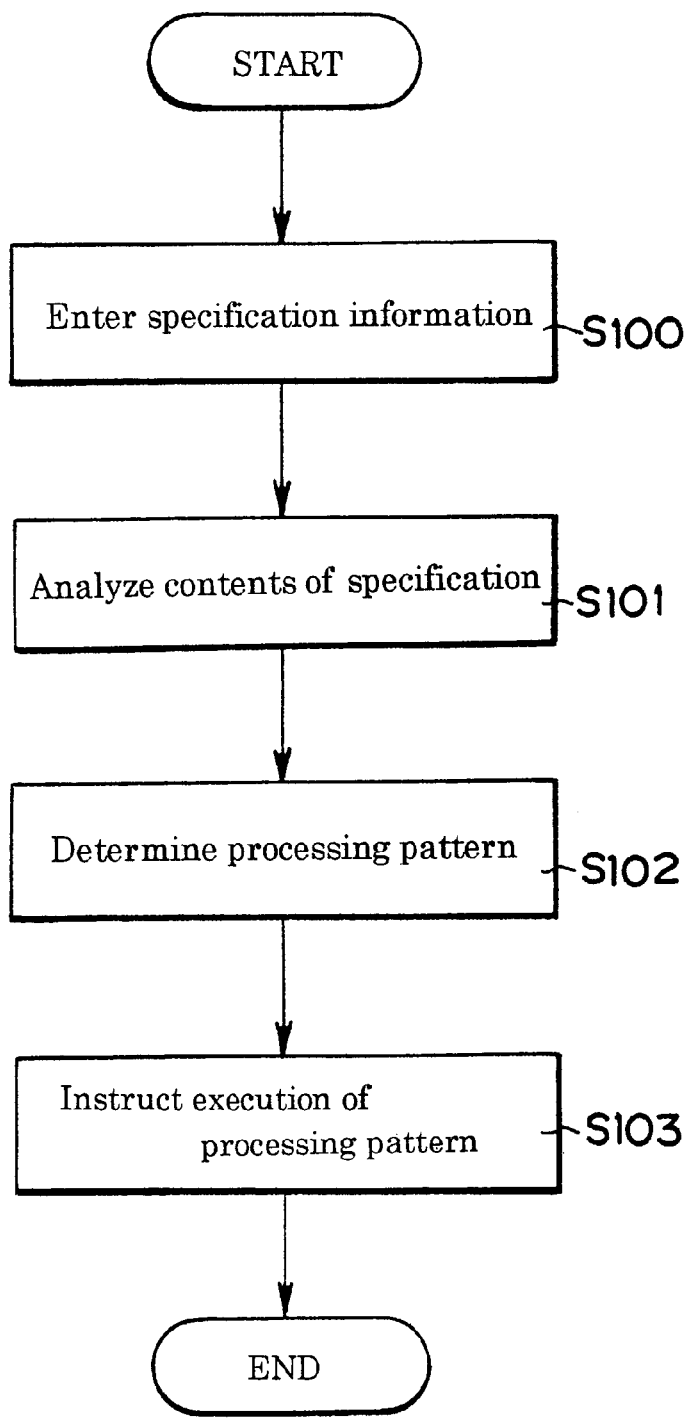
FIG. 1 is a control flow in the present invention.

A control flow for providing instructions to a sample distributor or a container feeding device according to the invention is shown in FIG. 1. Specification information, such as material conditions or material kinds, is entered S100 and analyzed to determine required processing S15. Based on the analyzed contents of at least the specification information, a processing pattern is determined S102 whereupon instructions for execution of processing are given to the sample distributor or container feeding device S103.

Figure 2:
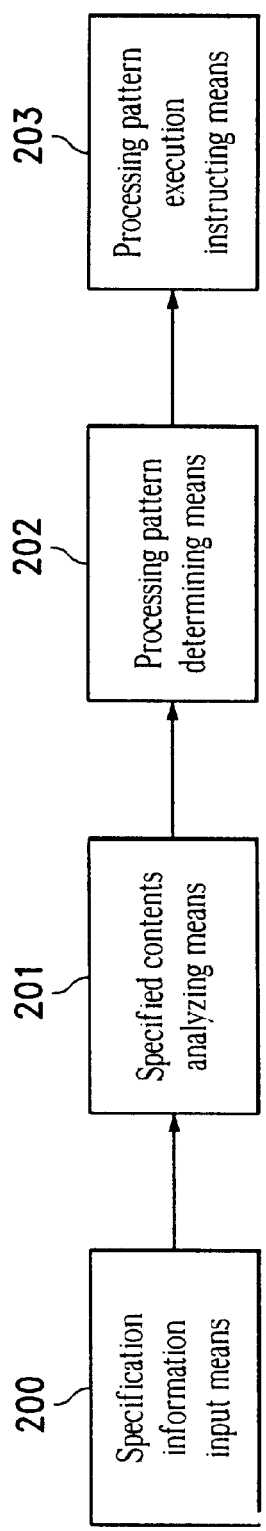
FIG. 2 is a control block in the present invention.

A control block in the present invention is depicted in FIG. 2. A specification information input means 200 inputs information by optically reading a work sheet (mark sheet), reading a floppy disk and CD ROM, inputting through keyboard or mouse, or inputting via communication. A specification content analyzing means 201 analyzes the contents of at least the specification information entered to determine required processing. Based on the analysis of the specification information, a processing pattern determining means 202 determines a processing pattern that the sample distributor or container feeding device must follow. A processing pattern execution instructing means 203 then gives instructions for executing the processing to the sample distributor or container feeding device.

Figure 3:
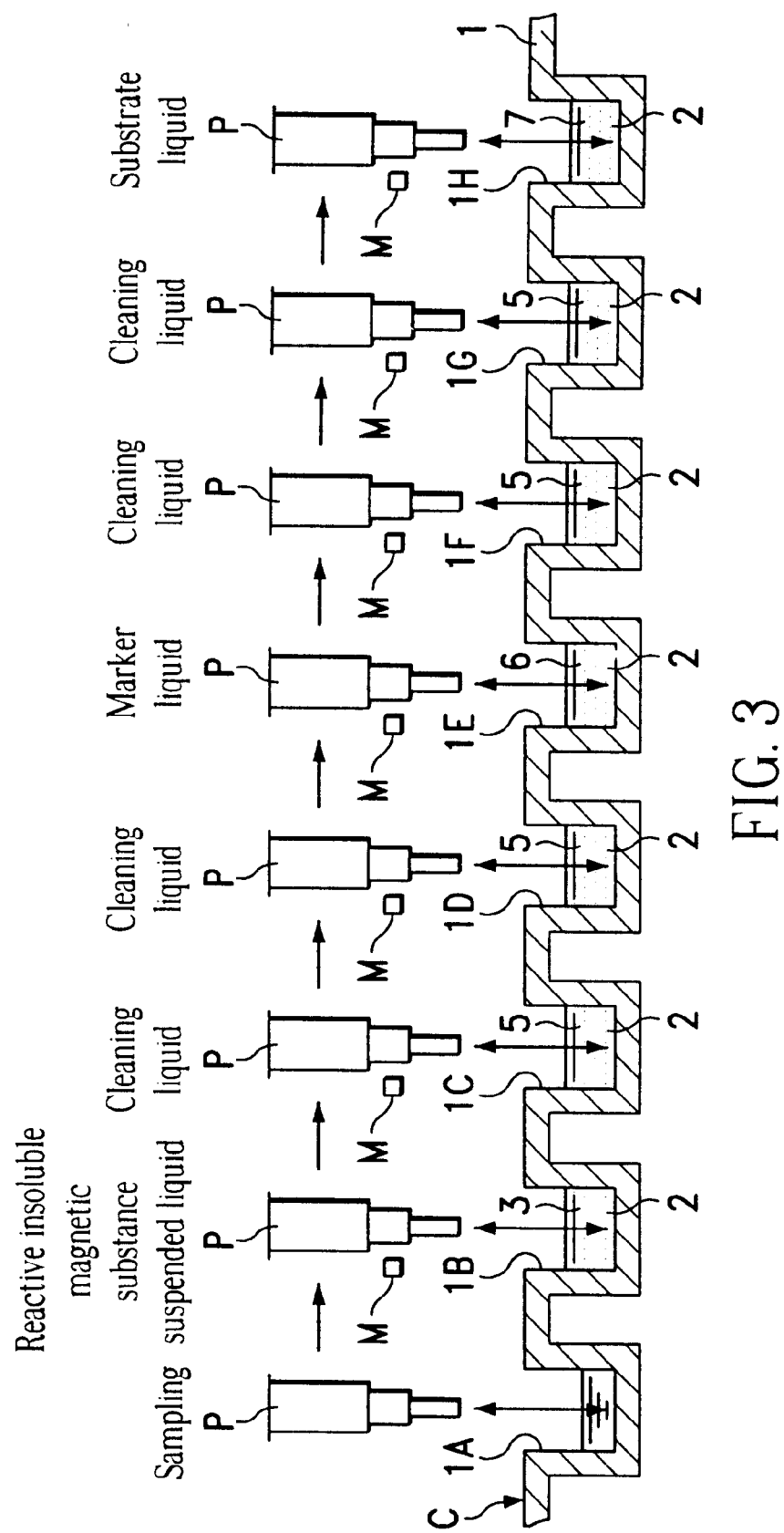
FIG. 3 is a process flow diagram showing schematically the process of controlling the magnetic particles by a sample distributor of this invention.

FIG. 3 shows the basic flow of process steps according to this invention.

In the figure, reference number 1 represents a container, which has liquid accommodating portions 1A–1H arranged in a line or in a loop or in a zigzag form. These liquid accommodating portions constitute an integrally formed container cartridge C. Over the container cartridge C a pipette tip P attached to the nozzle is moved to a predetermined position where it draws up or discharges a required amount of liquid to and from each of the liquid accommodating portions 1A–1H. During this process, a magnet M is put close to the liquid passage of the pipette tip P to attract magnetic particles 2 contained in the liquid and thereby separate them in the separation region from the liquid, and is then moved away from the liquid passage to allow the magnetic particles 2 to be suspended in the liquid.

The liquid accommodating portion 1A is preliminarily supplied with a sample liquid. The liquid accommodating portion 1B is supplied beforehand with a predetermined amount of a reactive insoluble magnetic substance suspended liquid 3 containing a reactive insoluble magnetic substance. The liquid accommodating portions 1C and 1D are supplied beforehand with a predetermined amount of a cleaning liquid 5. The liquid accommodating portion 1E is supplied beforehand with a predetermined amount of a marker liquid. The liquid accommodating portions 1F, 1G are supplied beforehand with a predetermined amount of the cleaning liquid 5. Further, the liquid accommodating portion 1H is supplied with a specified amount of a substrate liquid. In this way, the conditions for conducting an assay are prepared in a preliminary stage.

As for the material of the reaction container 1, when light needs to be shielded as in CLIA and CLEIA assay, the reaction container 1 is made of an opaque material that prevents the contents of the individual containers from being affected by luminescence of one another. When light needs to be transmitted as in a light transmission level measurement in the EIA assay, the reaction container 1 is made of a transparent material at least at the bottom.

An assay means for immunochemical inspection according to this invention will be explained in an example case where the luminescence is measured by an optical measuring device.

First, a sample liquid, which was supplied in the preliminary step to the liquid accommodating portion 1A, is drawn into the pipette tip P in a predetermined amount.

Next, the pipette tip P containing the sample liquid is moved over the liquid accommodating portion 1B that contains the reactive insoluble magnetic substance suspended liquid 3, into which the sample liquid is fully discharged from the pipette tip P. Then, the mixture liquid of the sample liquid and the reactive insoluble magnetic substance suspended liquid 3 is repetitively drawn and discharged to and from the pipette tip P (this process is referred to as a liquid suction and discharge) to produced a uniformly agitated mixture of magnetic particles 2. After an elapse of a predetermined time, the incubated mixture is drawn fully or in a predetermined amount into the pipette tip P.

Figure 4:
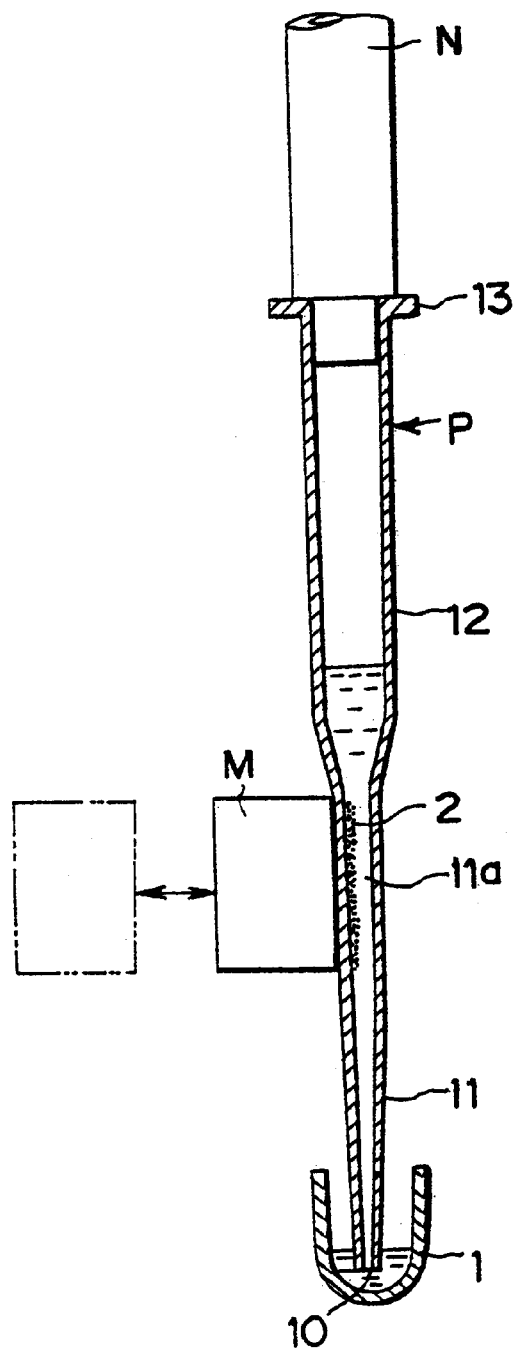
FIG. 4 is a schematic, enlarged vertical cross section showing the pipette tip of this invention and its associated components.
Figure 5A:
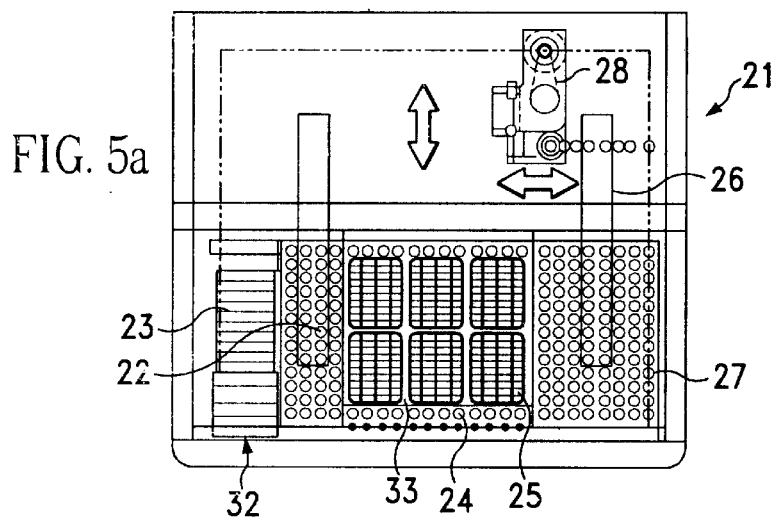
FIGS. 5a–5b is an example configuration of the apparatus as the first embodiment of this invention, suitably applied for immune assay based on the chemical luminescence method.
Figure 5B:
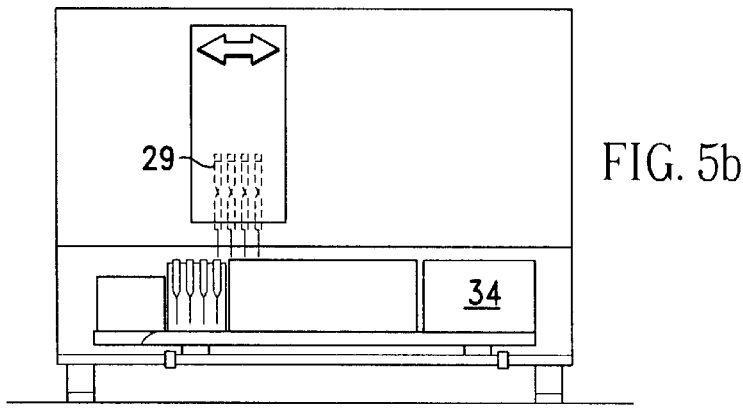
Figure 5C:
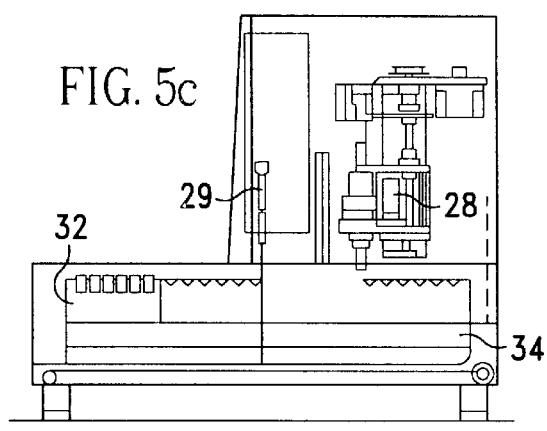
Figure 5D:
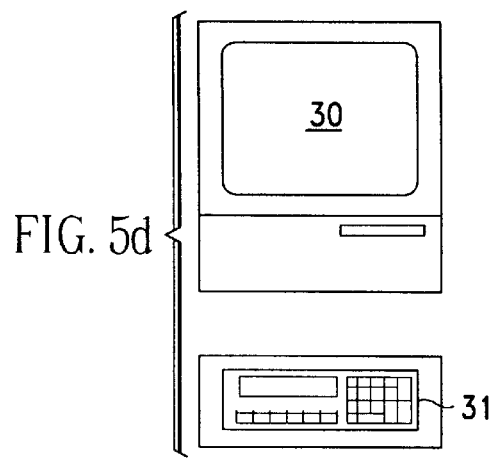

When the mixture liquid passes through a separation region 11a provided in a liquid passage 11 of the pipette tip P shown in FIG. 4, the magnetic particles 2 suspended in the mixture liquid drawn into the pipette tip P are attracted to the inner wall of the separation region 11a of the liquid passage 11 by the magnetic force of a magnet M arranged on the outside of the pipette tip P. The suction height of the mixture liquid is such that when all the mixture liquid is drawn up, the bottom level of the liquid is higher than the lower end of the separation region 11a of the liquid passage 11, i.e., the lower end of the magnet M, to ensure that the magnetic particles 2 drawn in can be completely arrested.

After the magnetic particles 2 are arrested in this manner, the mixture liquid removed of the magnetic particles 2 is discharged into the liquid accommodating portion 1B and drained out, with only the magnetic particles 2 remaining in the pipette tip P. At this time, because the magnetic particles 2 are wet, they stay attached to the inner surface of the separation region 11a of the liquid passage 11 of the pipette tip P. If the pipette tip P is moved or transported, the magnetic particles 2 will not come off easily.

Next, the pipette tip P with the arrested magnetic particles 2 is transferred to the next liquid accommodating portion 1C, where it draws in a cleaning liquid 5. At this time, the magnet M is moved away from the separation region 11a of the pipette tip P to release the magnetic particles 2. By performing the suction and discharge operation on the cleaning liquid 5, the magnetic particles 2 are again suspended and can be washed fully and efficiently.

The liquid drawing is performed in such a way that a part of the liquid is left in the container. This is to prevent generation of bubbles caused by air drawn in. It is important that the level or amount of the cleaning liquid be controlled at a level higher than the previous level of the solution to be cleaned.

After the liquid suction and discharge operation is finished, the pipette tip P slowly draws in all the cleaning liquid 5 from the liquid accommodating portion 1C. At this time, the magnet M is brought close to the pipette tip P to arrest all the magnetic particles 2 suspended in the cleaning liquid 5 drawn in. Then, the cleaning liquid 5 cleared of the magnetic particles 2 is discharged into the liquid accommodating portion 1C and drained out, with only the magnetic particles 2 remaining in the pipette tip P.

Next, the pipette tip P with the arrested magnetic particles 2 is transferred to the next liquid accommodating portion 1D, where it draws in a cleaning liquid 5. Then, the same procedure that was performed in the liquid accommodating portion 1C is carried out to clean and arrest the magnetic particles 2.

Next, the pipette tip P with the arrested magnetic particles 2 is moved to the next liquid accommodating portion 1E, where it draws in the marker liquid 6. At this time, the magnet M is moved away from the pipette tip P to release the magnetic particles 2. Then the marker liquid 6 is repetitively drawn in and discharged to make uniform the reaction between the magnetic particles 2 and the marker liquid 6.

A predetermined time after the liquid suction and discharge operation has been finished, the pipette tip P slowly draws in the entire marker liquid 6 from the liquid accommodating portion 1E. At this time, the magnet M is brought close to the pipette tip P to attract the magnetic particles 2 suspended in the marker liquid 6. The marker liquid 6 except for the magnetic particles 2 is discharged into the liquid accommodating portion 1E and drained out, with only the magnetic particles 2 remaining in the pipette tip P.

After this, the pipette tip P with the magnetic particles 2 is moved to the next liquid accommodating portion 1F, where it draws in a cleaning liquid 5 and performs the cleaning and arresting of the magnetic particles 2 in the same way as in the liquid accommodating portions 1C, 1D. To cause the magnetic particles, which were arrested and became a pellet, to be fully suspended in the liquid, the liquid is quickly drawn in and discharged about 10 to 15 times for agitation. Then, a cleaning liquid 5 in the next liquid accommodating portion 1G is drawn in, in the same manner as in the liquid accommodating portion 1F to clean and arrest the magnetic particles 2.

Then, the pipette tip P is transferred to the liquid accommodating portion 1H. If the sample continues to emit light after being mixed with a substrate liquid and takes a certain time before the luminescence becomes stable, as in the CLEIA assay, the pipette tip P draws in a substrate liquid 7 contained in the liquid accommodating portion 1H. At the same time, the magnet M is moved away from the pipette tip P to release the magnetic particles 2 so that the reaction between the magnetic particles 2 and the substrate liquid 7 can be made uniform by the liquid suction and discharge operation.

Then, a predetermined time after the liquid suction and discharge operation, the luminescence of the sample is measured.

FIG. 4 shows the detail of the surrounding of the pipette tip in this embodiment. Here, reference numeral 1 represents a container used to mix a required amount of reagent for reaction with a sample and a predetermined amount of sample or magnetic particles 2. The container 1 may be formed as a container cartridge C having a number of containers 1 integrally formed to allow efficient work. The capacity of each container 1 (1A–1H) is several tens to several hundred microliters.

Designated P is a pipette tip, made of polypropylene, which is a tube tapered off toward the tip portion 10 that is used to draw in or discharge liquid. The pipette tip has a cylindrical liquid passage 11 uniform in diameter along its length and directly connected to the tip portion 10; a separation region 11a in the liquid passage 11 that is applied with a magnetic field; and a cylindrical reservoir portion 12 connected to the liquid passage 11 through a cone portion whose taper inclination is less than 7(. The reservoir portion 12 has a flange 13 formed along its opening edge to prevent deformation of the opening. The liquid passage 11 having the separation region 11a is about 4 mm in outer diameter and less than 1 mm thick and is so formed as to ensure that a liquid having a constant cross-sectional area flows at a substantially uniform speed over the entire length of the liquid passage. The tip portion 10 is formed narrow, about 1 mm in outer diameter, about 0.5 mm in thickness and 20–30 mm in length, and is moderately expanded from the end toward the liquid passage 11.

Designated N is a nozzle of the distribution unit, which is provided at the front end portion of the unit (not shown) and whose end is so formed as to be able to be inserted into or removed from the opening of the reservoir portion 12 of the pipette tip P. The interior of the pipette tip P is made negative or positive in pressure by the suction and discharge operation of the distribution unit trough the nozzle N.

Denoted M is a magnet, which is placed in contact with or held several millimeters from the outer surface of the separation region 11a of the liquid passage 11 of the pipette tip P in order to arrest the magnetic particles suspended in a liquid on the inner surface of the separation region 11a of the liquid passage 11.

The distribution unit (multi-nozzle type is referred to as a nozzle unit; see FIG. 6) 29 drives a stepping motor (not shown) according to a control signal from a control unit and converts the rotating motion of the shaft into a reciprocating motion of a piston 29b to supply and exhaust air to and from the pipette tip P through the nozzle N. The distribution unit 29, by using a distribution tip (not shown), pours a sample into the liquid accommodating portion 1A from a reaction container (not shown). The distribution unit 29, after being transferred immediately over each container 1B–1H, can be moved vertically or in parallel or in plane freely for suction and delivery.

Now, in a system using the above-mentioned pipette tip P, preferred embodiments will be explained in detail by referring to the accompanying drawings.

First Embodiment

FIG. 5 shows one example configuration of a system of this invention that is suited for immune assay based on the chemical luminescence method.

This system comprises a system unit 21 that includes processing mechanisms and a controller 34 for controlling the mechanisms by a built-in computer; a keyboard 31 used to enter instructions to the system unit; and a display 30 for displaying information.

The system unit 21 comprises a stage 32 that mounts a variety of containers and can be moved back and forth with respect to the system unit; a distribution unit 29 provided above the stage 32, which can be moved laterally and vertically with respect to the system unit; and an optical measuring unit 28 provided above the stage.

Figure 6:
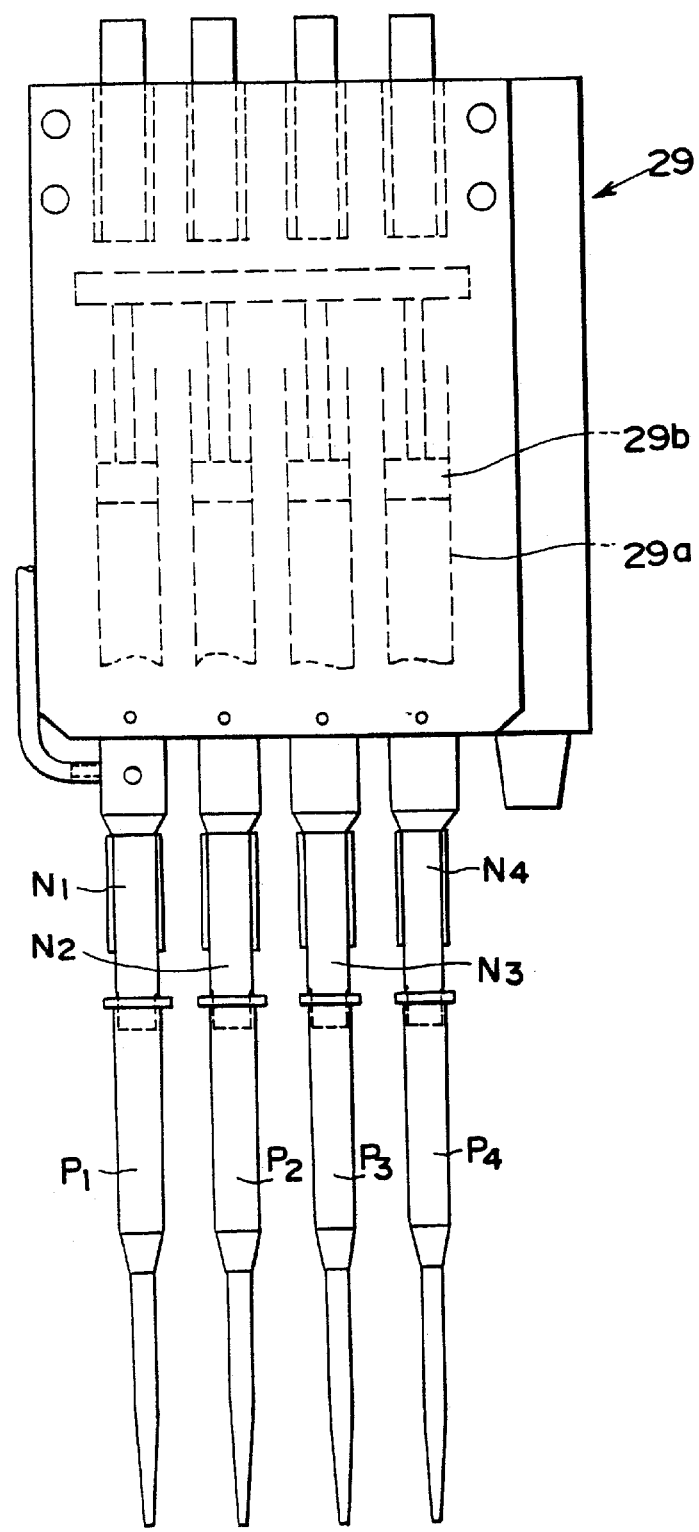
FIG. 6 is a front view of a four-pipette sample distribution unit applicable to this invention.

The distribution unit 29, as shown in FIG. 6, has four nozzles N arranged in line at predetermined pitches. These four nozzles N can be driven simultaneously. The front ends of these nozzles N are removably attached with the pipette tips P. The distribution unit 29 has cylinders 29a inside at positions corresponding to the nozzles N. In these cylinders 29a there are provided four ganged pistons 29b that perform the air supply and discharge operation simultaneously.

For lowered cost and simplicity, the distribution unit 29 used in this embodiment does not allow independent operation of each of the pistons in the cylinders and makes the four ganged pistons move at the same time.

The nozzles N of the distribution unit 29 may be formed integral with the cylinders or separately formed. Even in the separate type, a high precision control is possible by forming the cylinder and the nozzle as a pair unit, reducing the horse as much as possible and minimizing the air gap.

There are two types of pipette tips P attached to the nozzles N of the distribution unit 29-a pipette tip P used for agitation, cleaning and arresting of magnetic particles 2 and a pipette tip P used for supplying reagent or the like. Further, there are a small-capacity pipette tip P (mainly for immune assay) and a large-capacity pipette tip P (mainly for DNA assay). In this system, the liquid passage 11 of the pipette tip P having the separation region Ha for arresting the magnetic particles 2 by the magnet is about 2–3 mm in inner diameter and its operation results are satisfactory. This inner diameter need only be such that the liquid flowing through this passage is under the influence of strong magnetic force sufficient to arrest the magnetic particles.

In arresting the magnetic particles 2, agitation is performed prior to the arresting as required. This is to agitate and mix sediments after incubation. The amount of liquid to be drawn in during the magnetic particle arresting operation is equal to the amount in the container plus an amount of liquid that can pass through the separation region 11a of the pipette tip P.

The speed, at which the liquid flows past the separation region 11a of the pipette tip P, is set at 13 (l/sec in this system. At this flow rate, the magnetic particles 2 are arrested satisfactorily. If the flow speed is slower, the arresting becomes more reliable. Considering a tradeoff with the processing power, however, an overall judgment is made to set an appropriate flow speed. The arresting speed varies depending on the kind of the magnetic particles 2 and the viscosity of reagent used.

Figure 7:
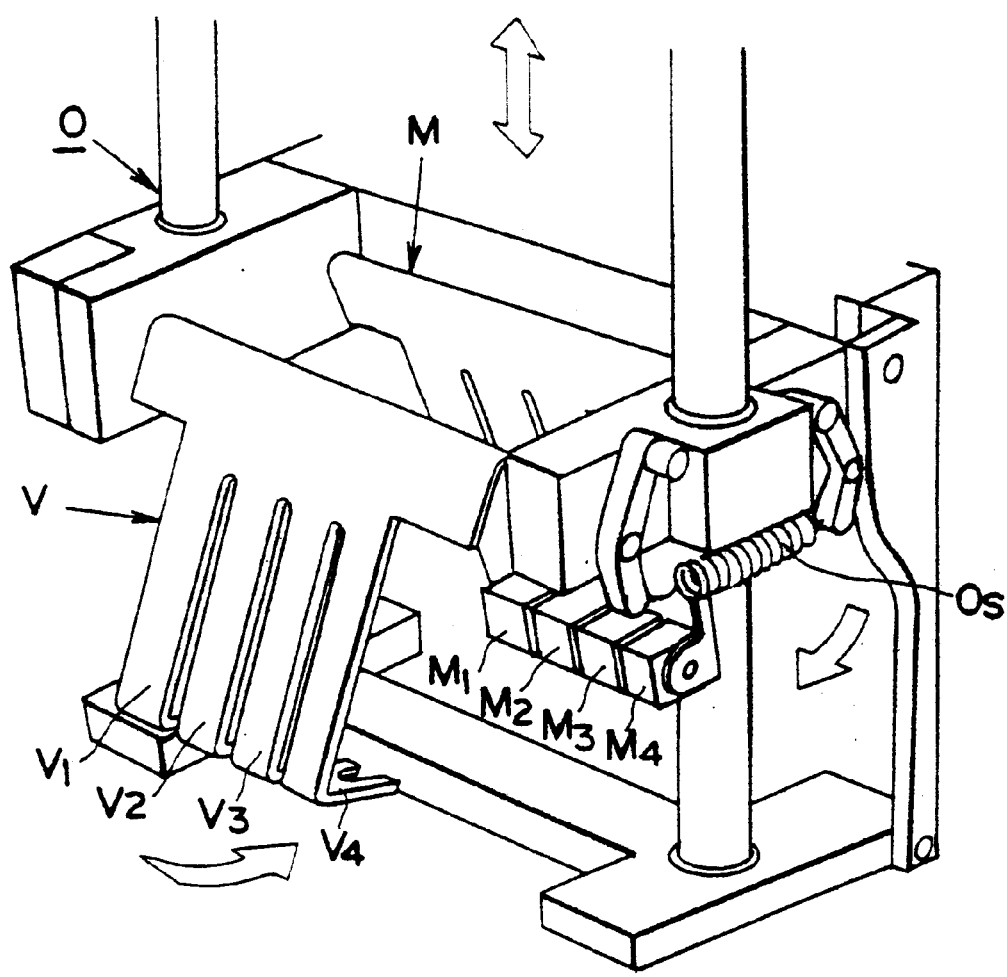
FIG. 7 is a perspective view showing an example configuration of a holder and a magnetic field source when the four-pipette sample distribution unit is used.
Figure 8:
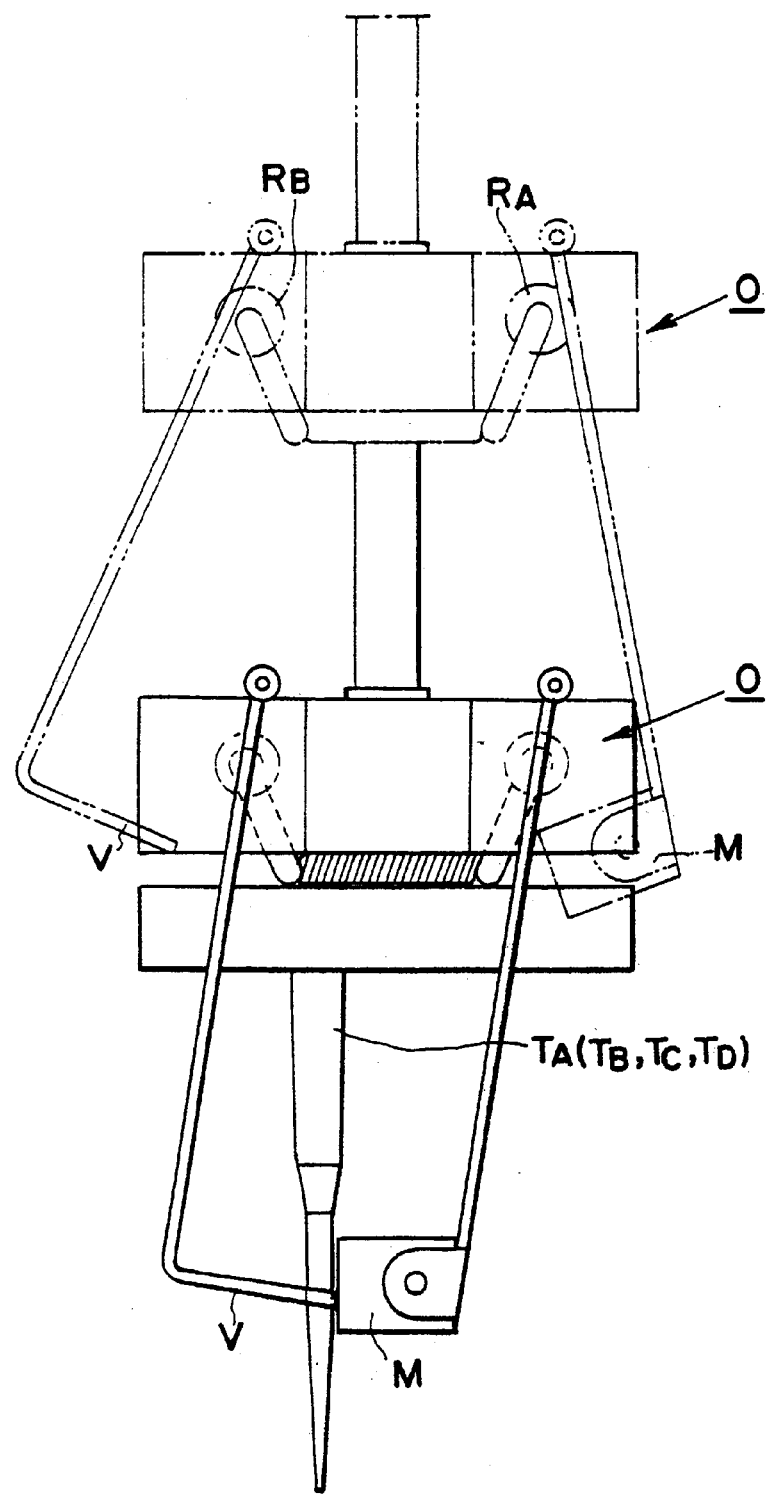
FIG. 8 is a schematic diagram showing the operation of the holder and the magnetic field source.

FIG. 7 and FIG. 8 show a magnet driving device suited for driving a magnetic field source M and a holder V when processing a liquid by using cylinders shown in FIG. 6. In this example, the magnetic field source M shaped like a comb and having magnet portions M1, M2, M3, M4 and the holder V shaped like a comb and having holder portions V1, V2, V3, V4 are pivotably mounted on a raise-lower mechanism O so that they can be opened and closed. As the raise-lower mechanism O is moved up or down, rollers RA, RB of the raise-lower mechanism O are closed, as shown in FIG. 8, to cause the magnetic field source M and the holder V to close in the tip holding direction by the action of a spring Os shown in FIG. 7. As a result, the magnetic field source M engage with the four pipette tips P1, P2, P3, P4 simultaneously, or the holder V and the magnetic field source M together hold the pipette tips.

With the magnetic field source M and the holder V constructed in this way, when liquid processing lines are separated by partition walls, it is possible to perform attraction, agitation and mixing of magnetic particles 2 or liquid suction and discharge at exactly the same timing among the four liquid processing lines, thus substantially improving the process efficiency with a simpler configuration. This invention is not limited to the above embodiment in which the magnetic field source M and the holder V are formed in a ganged four-process-line configuration, but it may also have a two-process-line configuration as needed.

In the distribution unit 29, one of the four ganged nozzles N1, N2, N3, N4 (for example, N1) is provided with a pressure sensor function. After the nozzle N1 is attached with a pipette tip P and the pipette tip P is lowered into the container, this pressure sensor detects the liquid level in the container.

Simultaneous performance among multiple process lines of such operations as separation, agitation and cleaning of magnetic particles is possible, provided that a predetermined amount of liquid is supplied in the reaction containers beforehand. However, prior to this process, a parent sample needs to be distributed. The parent sample is stored in a vacuum blood sampling tube or the like and there are variations in its liquid level. Hence, when the four ganged nozzles are used, one of the nozzles is provided with a liquid level detection function by a pressure sensor, so that this nozzle can be used to distribute the parent sample. With the parent sample distributed, the four nozzles can then be used by the distribution unit for the simultaneous processing Therefore, when the parent specimen is distributed, the pipette tip is of course attached only to the nozzle N1. At this time, it is necessary to control the positions of a pipette tip rack for stock and the pipette tip P. The nozzle N1 can also be provided with a container bottom detection function. When the nozzle N1 attached with the pipette tip P is lowered in a bottom landing mode and the end of the pipette tip P contacts the bottom, the nozzle N1 is elastically moved rearward. This backward movement is detected to determine when the bottom is reached.

When the bottom is recognized in this way, the nozzle N1 is lifted so that the front end of the nozzle is out of contact with the container. With the front end of the pipette tip P kept within a short distance (0.1–0.2 mm) from the container, the liquid suction and discharge operation is performed. This arrangement allows the whole liquid containing the magnetic particles 2 to be drawn in smoothly without clogging the pipette tip. For a small amount distribution, it is possible to control the distance between the end of the pipette tip and the bottom of the container at a very small value when the liquid is delivered.

The nozzle N is also provided with a tray mechanism that receives droplets should they fall from the pipette tip P when the nozzle N attached with the pipette tip P is moved. This mechanism is provided close to the distribution unit 29. When the distribution unit 29 is lifted and the front end portion of the pipette tip P moves past the position of the tray, the tray is pushed out to a position below the pipette tip P to receive falling droplets, if any.

On the stage 32 shown in FIG. 5, there are provided a reagent unit 23 in which a plurality of reagent containers having a rectangular opening are arranged; a tip rack 22 in which a plurality of rows of four-pipette-tip assemblies P are installed; and a container tray 33 in which are arranged six sets of four container cartridges 25, each container cartridge having a plurality of holes.

Further on the stage 32 are provided a pipette tip unit 24 in which pipette tips are temporarily stored for later reattachment; a reaction container area 27 where a plurality of samples (in this example, 48 samples) are accommodated in containers; and a measured cell area 26 where samples that have finished processing are stored.

Inspection systems for immune bodies, DNA, viruses and germs require a constant-temperature state for nearly all reactions. This apparatus performs comprehensive temperature control and keeps the preliminarily distributed reagents at a specified temperature using Peltier devices for heat panel and heat block or for cooling.

The DNA assay in particular involves many processes in which a sample is kept at a relatively high temperature or subjected to a heat cycle with a specified temperature difference. With this apparatus, the liquid can be temperature-controlled easily and with high precision simply by transferring the liquid or magnetic particles into a container that is preheated to a predetermined temperature.

Below the reagent unit 23 is provided a Peltier device, which cools the reagent at a predetermined temperature. A heat block is arranged below the container tray 33 to keep the liquid in the container cartridge 25 at a specified temperature.

The optical measuring unit 28 shown in FIG. 5 has a PMT (photomultiplier tube) as a means for counting photons. The PMT moves up or down and counts photons by enclosing the sample and shielding external light. Depending on the items for measurement, a transmission method, a spectrum method or a specific opacity method may be applied. To cope with these measuring methods, the container cartridge 25 has its measuring holes formed transparent and the optical measuring device is constructed in conformity with the measuring items.

For the magnetic particle liquid that has undergone a series of reactions, the CLIA method results in a short light emitting time when a trigger reagent (H2O2 for instance) is injected. Hence, because the trigger reagent (H2O2 for instance) is required at time of measurement, a distribution nozzle for the trigger reagent must be provided.

With the CLEIA method, on the other hand, the luminescence becomes stable producing a plateau reading with elapse of a certain time after the reaction. The CLEIA method therefore does not need a trigger reagent. The apparatus of this invention has a trigger reagent distribution nozzle and employs a configuration of PMT+trigger reagent distribution nozzle holder+reaction cartridge. This arrangement allows the operator to choose between the use and the removal of the trigger reagent nozzle holder. In addition, this apparatus has a complete light shielding structure and can be used for either CLIA method and CLEIA method.

Next, the fundamental control configuration of the controller 34 will be explained.

Figure 9:
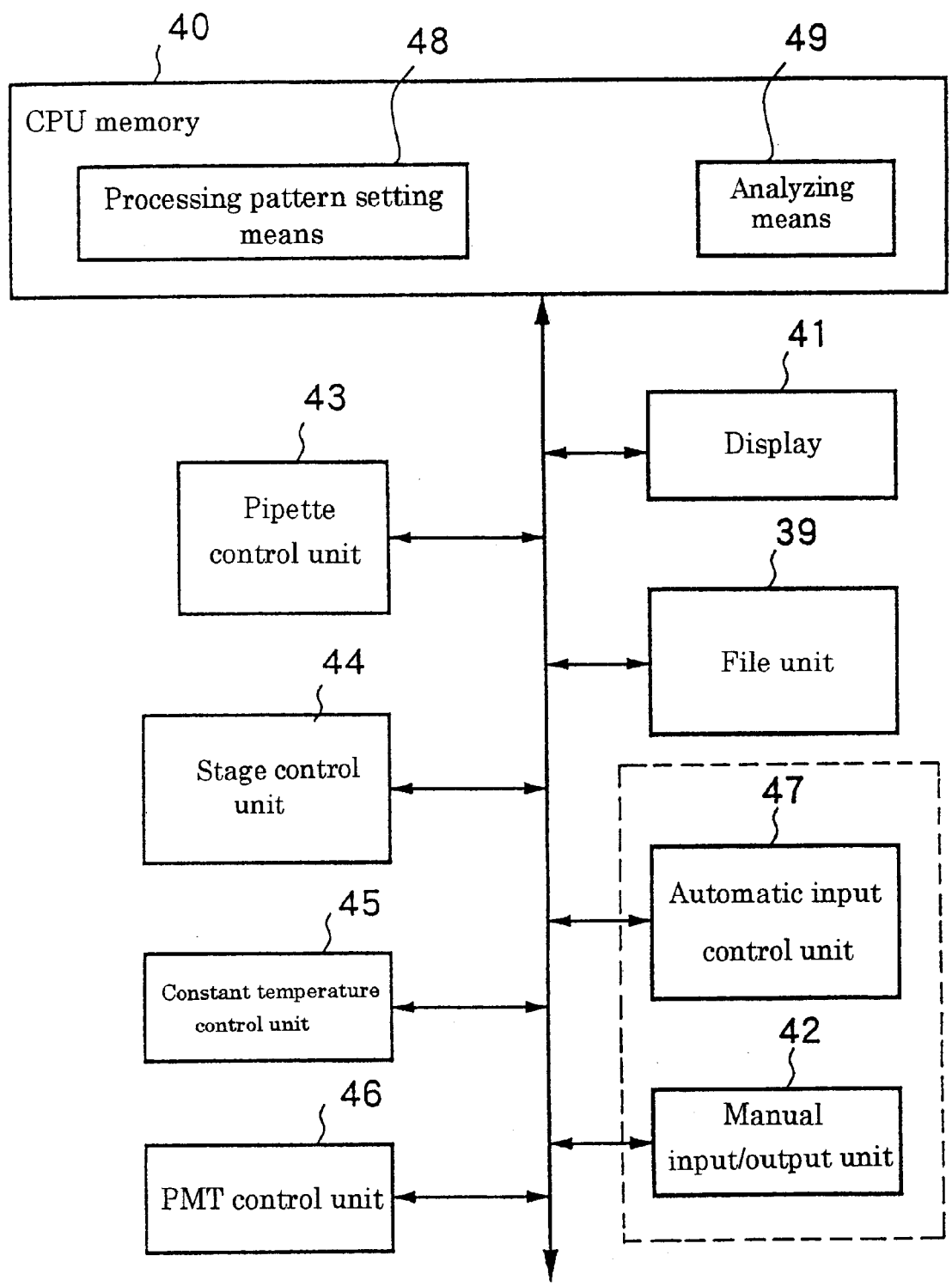
FIG. 9 is a block diagram showing the control system of this apparatus.

As shown in FIG. 9, this controller 34 comprises: a CPU and memory 40 that performs a variety of controls on the system unit 21; a display unit 41 that controls the display 30 for displaying the results of analyses; an automatic measurement item input control unit 47 for controlling the input of a work sheet (a kind of mark sheet; here we call it a work sheet as it specifies the contents of work to be done) read by an optical mark reader and for controlling the input of information from loaded floppy disks and CDROMs and through communications, the measurement item input control unit being used as an item specification means to automatically specify the items that can be processed successively using the same container cartridge; a manual input/output unit 42 for controlling the keyboard 31 used to enter data; a pipette control unit 43 for controlling the distribution unit 29; a stage control unit 44 for controlling the stage 32; a constant-temperature control unit 45 for keeping the heat block provided under the container plate at a constant temperature and for controlling the temperature of the Peltier device below the reagent unit 23; and a PMT control unit 46 for controlling PMT of the optical measuring unit 28 and others.

A part of the automatic input control unit 47 and of the manual input/output unit 42 corresponds to the specified information input means.

The CPU and memory 40 includes a processing pattern setting means 48 for setting a processing pattern for the items specified by a program through the automatic measurement item input unit 47 according to the data contained in each item, such as the number of cleaning processes, the number of samples, the number of divided samples, a total process time for each item, a time taken by each process contained in each item, and container cartridge position; and an analyzing means 49 for analyzing the result obtained through the PMT control unit 46.

Stored in the memory beforehand are the contents of each item and a program specifying the procedure for processing each item. The CPU and memory 40 of course stores various other control signals associated with this apparatus.

Figure 10:
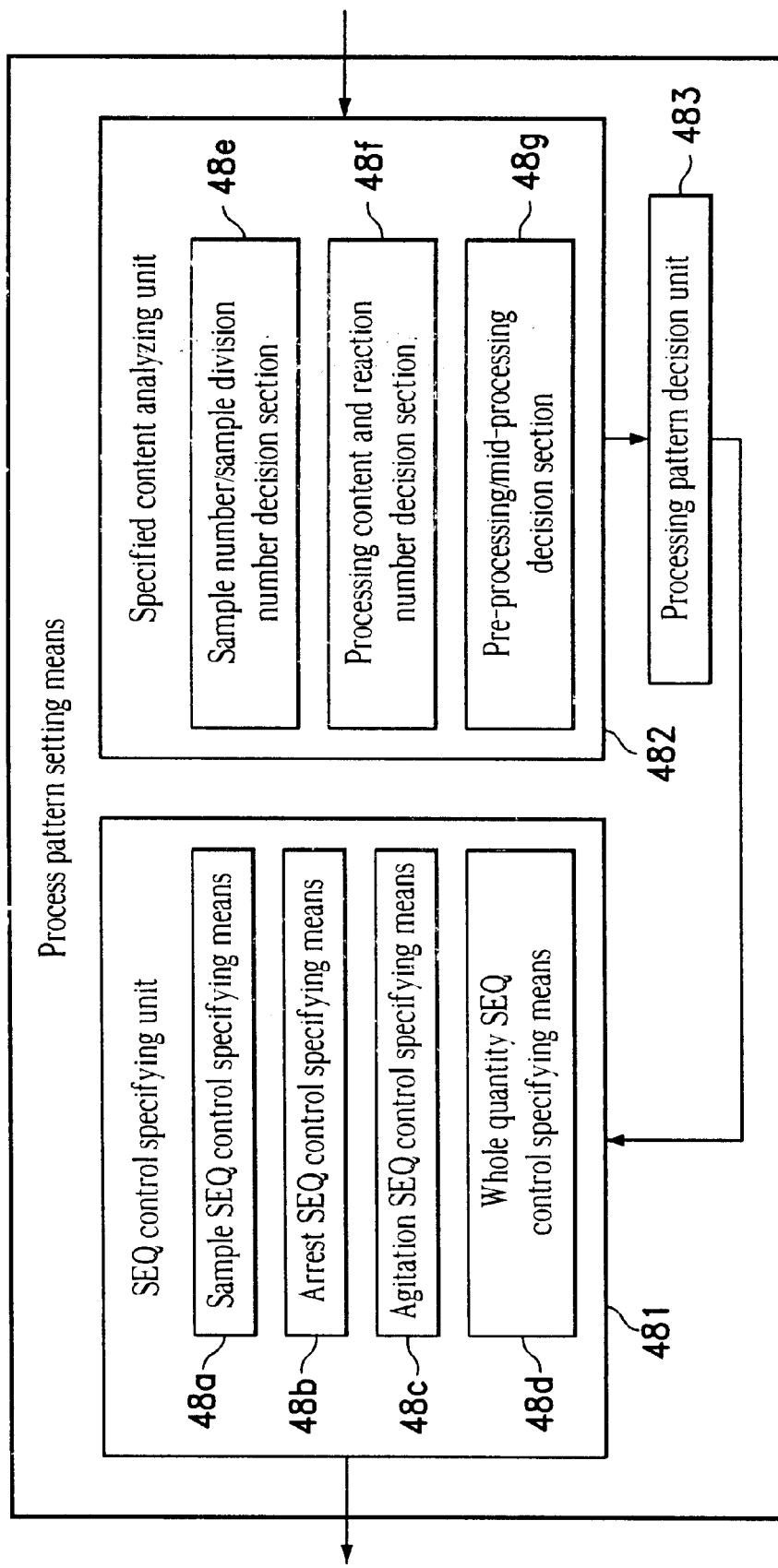
FIG. 10 is a block diagram showing the processing pattern setting means according to this invention.

FIG. 10 shows the detail of the processing pattern setting means 48.

The processing pattern setting means 48, as shown in the figure, includes a specified content analyzing unit 482 for analyzing the contents of the work sheet read from the automatic input unit 47; a processing pattern decision unit 483 for determining the processing pattern that the distributor or the container feeding device should follow, according to the specified contents that were analyzed; and a SEQ control specifying unit 481 for specifying the execution of processing according to the processing pattern that was determined for the distributor or the container feeding device.

Further, the specified content analyzing unit 482 includes a sample number/sample division number decision section 48e that checks the number of samples or the number of divided samples from e.g. the read work sheet; a processing content and reaction number decision section 48f that checks the substance conditions, reaction conditions or operation conditions from the inspection request information contained in the work sheet or from information contained in a floppy disk or entered from keyboard; and a pre-processing/midprocessing decision section 48g that checks if there is any request calling for preprocessing or mid-processing.

Here, the "pre-processing" and "mid-processing" mean a preliminary processing that distributes required amounts of specified reagents or the like to specified containers immediately before the intended processing, rather than preparing required quantities of specified reagents in the containers beforehand. This embodiment allows the request for pre-processing to be made through the automatic input control unit 47.

The "pre-processing" refers to carrying out this preparation prior to the execution of the intended processing and the "mid-processing" signifies distributing required amounts of specified reagents to specified containers during the course of the intended processing. In this embodiment the pre-processing and the midprocessing can be specified from the automatic input unit 47.

The SEQ control specifying unit 481 includes a sample SEQ control specifying means 48a that makes a request for the distributor to draw in a sample and discharge it into a specified container (including agitation as needed); an arrest SEQ control specifying means 48b that makes a request to bring the magnet provided in the distributor close to the pipette tip to attract the magnetic particles bonded to a target substance and suspended in the liquid to the inner surface of the pipette; an agitation SEQ control specifying means 48c that makes a request to cause a pipette tip to perform a high-speed suction and discharge to agitate the liquid; and a whole quantity SEQ control specifying means 48d that requests drawing in and discharge the whole quantity of liquid in the container. The setting of the processing pattern depends on whether the number of samples is one or two or more and whether there are divided samples.

When the number of samples is one, the processing specified in the work sheet is executed as is. When two or more samples are used or there is a sample division, the processing pattern decision unit 483 determines the processing pattern according to the specification of the work sheet in such a way as to carry out as much processing in as short a time as possible, i.e., to increase the process efficiency.

If the distribution unit 29 is made to devote itself to the processing of one item until the processing of one container cartridge is finished, by pegging the container cartridge at the distribution position, the processing time for all samples, which equals to the processing time for each item multiplied by the number of samples, becomes very large.

Most of the processing time, however, is spent for incubation (constant temperature reaction), during which time the distribution unit 29 is idle. Hence, using this idle time for performing other processing can reduce the overall processing time.

That is, the reaction process for one item and the incubation time in that process are recognized in the form of a time chart; and the distribution unit manages a plurality of reaction processes in the form a processing pattern with time delays between them and performs the reaction processes in parallel. This arrangement allows efficient control of the reaction processes.

The conditions that permits such a control are that the minimum incubation time that can be set $t_{min}$ is larger than the total working time of the entire processing consisting of a plurality of reaction processes (excluding the incubation time) T. That is, $$T \leq t_{min} \quad (1)$$

With this condition met, one distribution nozzle can perform the same processing on one other target substance such as sample in the incubation time. The second condition is that the incubation time t to be set is an integer times the minimum incubation time $t_{min}$. That is, $$t = n \times t_{min} \quad (2)$$

This condition allows one distribution nozzle to perform the same processing on n other samples in the incubation time.

When it is possible to make control requests not only to the distributor but also to the container feeder, the same process need only be repeated to improve the processing efficiency because this permits the use of the same program and eliminates the need for repetitive reading of program. The improved efficiency can also be achieved by classifying the items and feeding the containers so that a group of the same or similar items is processed en masse because this arrangement minimizes the operation of the pipette device.

In other words, the same process step is carried out for a plurality of the same items in a plurality of container cartridges. After this group of process steps is finished, the control moves to the next process step. With this arrangement, the distribution unit 29 can perform the same process step on the number of the container cartridges that can be processed within the incubation time. In this way, the processing efficiency can be enhanced.

Considering the above, the processing pattern setting means 48 of this embodiment determines the processing pattern. The processing pattern setting means 48 sets the most efficient processing pattern for a specified item and, according to the processing pattern thus set, specifies control to the stage control unit 44, the pipette control unit 43, PMT control unit 46 and the constant-temperature control unit 45.

The pipette control unit 43 has a portion for controlling the magnet, a portion for controlling the holder, a portion for controlling the suction and discharge operation, and a portion for controlling the movement along X, Y and Z axis.

The operations of the distribution unit 29 and the stage 32 in this apparatus are all controlled by the controller 34. Based on the directions given by the controller 34, various processing are performed. Individual processing contents are read through the automatic measurement item input unit 47, stored in the file area 39 of the controller 34 and retrieved into the CPU memory 40 as required.

FIG. 11 shows a page 41a on a screen illustrating the example contents of various controls registered in the form of parameters.

Here, numbers given on a line of the "HOLE" item in an item column 41b represent the hole positions in the container cartridge 25. A "STEP" item represent the kind of reagents that are supplied in the holes beforehand. "Fe" denotes magnetic particles, "Cl." means a cleaning liquid, and "Co" designates a marker liquid. The line of "Reagent 1" shows the registered amounts of reagents to be supplied into the respective holes. Where the pre-processing is specified, the distribution unit 29 pours a specified amount of the registered reagent into the holes of the container cartridge 25. When the pre-processing nor the midprocessing is specified, this means that the required amounts of reagents were supplied beforehand.

On the line "Sample" are shown amounts of samples to be poured into respective holes.

Agitation is carried out the number of times that is registered in the "Agitation times" item. This agitation consists of drawing a liquid from the container into the pipette tip P and discharging it out into the container and repeating this process.

Further, the agitation is given an appropriate consideration. That is, the liquid to be agitated normally has a solid substance or highly dense matter deposited at the bottom. In the agitation process the front end of the pipette tip P is lowered to nearly the bottom surface of the container, so that if in this state a sudden, rapid suction is performed, sediments will collect in the narrow front end portion of the pipette tip P, clogging it. To avoid this, the pipette tip P draws in the liquid slowly at first, at a rate that will alleviate concentration of sediments.

As a result, the sediments are smoothly drawn in and after a required amount of liquid is taken in, it is discharged at a similarly slow rate, thus mixing the sediments in the liquid. This is followed by a rapid suction and discharge operation, thus achieving reliable and swift agitation.

The rate of suction and discharge is registered as a pulse motor speed that drives the suction pump. In that case, suction is registered as a (+) speed and discharge as a (−) speed.

The agitation is performed to mix the magnetic particles 2 and the reagent completely or to release the magnetic particles 2 from the inner surface of the pipette tip P to which they are adhering. Normally agitation is done at least two times. The number of times that the agitation is carried out is determined appropriately according to the kind of the reagent used and of the magnetic particles 2. The magnetic particles 2 can also be released from the pipette tip P by using a cleaning liquid. In this case, too, the separation is achieved by the repetitive suction and discharge of the liquid, which is practically the same as the agitation operation.

The agitation (cleaning) speed is preferably set faster than the suction and discharge speed during the separation process to release the magnetic particles 2 from the pipette tip P in a short period of time. But too fast an agitation speed will result in the failure of the liquid to follow the operation speed (the liquid cannot enter the front end portion of the pipette tip P as fast as the suction force changes). Too slow a speed will result in the failure of the magnetic particles 2 to be released from the pipette tip P. The agitation (cleaning) speed is changed according to the viscosity of reagent and the kind of magnetic particles 2. The normal agitation (cleaning) speed is set at around 300 $\mu$l/sec as the amount of liquid passing through the pipette tip P.

The "INC second" item specifies the incubation time, during which time the distribution unit 29 can perform processing on other container cartridges 25.

In this embodiment, as is evident from the fact that the "INC second" is set for the first hole and the third hole, reaction is performed twice in this embodiment. The specified content analyzing unit 482 decides that this embodiment uses a two-step method with the reaction performed in two steps.

When a flag is set in the "arrest" item, this specifies the omission of the agitation operation immediately before the arresting operation and the execution of a high-speed pumping with the magnet brought close to the pipette tip.

Item 41c, "Sample SEQ, arresting SEQ, agitation SEQ, whole quantity SEQ" item, is registered with sequence numbers, according to which processing is performed. Hence, the order of processing can easily be changed, making it possible to deal with a variety of inspections.

When two or more samples are used or there is a sample division, item 41d and item 41e are required. In this case, either the items 41d, 41e or the "INC second" item is automatically determined by the processing pattern determining unit according to the number of samples, the number of sample divisions, the contents of processing and the number of reactions, or according to the simulated operation of the distributor and the pre-registered data; it is not an item that is set on the work sheet by an operator through the automatic input control unit.

The time from the start of the processing to the start of the first incubation, the net time in the process "1" of FIG. 11, is set as "A." The net time from the end of the first incubation to the start of the second incubation, the net time of the process "2" to "6" of FIG. 11, is taken as "B." The net time from the end of the second incubation to the end of the processing, the net processing time of the process "7" to "14", is taken as "C." The magnitudes of A, B and C can be determined by performing the simulated operation of the distributor and measuring these times.

Hence, by using the equation (1), i.e., $A+B+C \leq t_{min}$, and the equation (2), i.e., $t = n \times t_{min}$, it is possible to determine the incubation time $t_{min}$ or t. Alternatively, whether the reaction process with the specified t or $t_{min}$ can be executed or not can be decided.

For example, if the net time for A is found to be 83 seconds, B 101 seconds and C 189 seconds, the incubation time is set to 373 seconds, thus allowing a plurality of samples or divided samples to be processed efficiently.

Conversely, the net processing times A, B and C may be determined by specifying the incubation time and setting the A, B and C times from the specified incubation time.

Further, "SA," "SB" and "SC" are times required by the mid-processing; they are the times found in idle periods in each process group "A," "B" and "C" that are set by the processing pattern decision unit 483 and used to supply reagents required in each process. These times are set slightly shorter than the times "A," "B" and "C." In other words, the times "A," "B" and "C" are set by the processing pattern decision unit 483 so that they are slightly longer than the "SA," "SB" and "SC" times.

Other possible specification may include pouring two kinds of reagents "Reagent 1, Reagent 2" to the same hole to make a mixture liquid of reagents.

Further, percentages of liquid drawn in from the container during the agitation and cleaning may be specified. For example, it is possible to draw 80% of the liquid, leaving the remaining 20% in the container.

The reason for leaving a part of the liquid is to prevent bubbles from being produced during agitation and cleaning, which may otherwise occur when air is drawn into the pipette tip When the amount of liquid to be agitated and cleaned is very small, it is possible to specify sucking air. Because the amount of liquid drawn in is very small, the whole liquid is held in the separation region of the pipette tip P by the air sucked in. Hence, the liquid can be moved up or down repetitively between specified locations in the separation region of the liquid passage of the pipette tip P (repetition of a small suction and discharge operation) for agitation.

The rate of liquid suction and discharge during agitation can be specified. For example, a polymer substance arrested by the magnetic particles 2 may easily separate from the magnetic particles because of its property. In that case, the agitation should preferably be performed at a low rate and thus a low speed can be specified.

The number of suction and discharge operations when arresting the magnetic particles 2 from the liquid can also be specified. The number of times that the particles are arrested is set at an appropriate value according to the kind of reagent contained in the liquid and the strength of magnetic attraction of the magnetic particles 2. Because in this apparatus the arresting of the magnetic particles 2 is carried out in the narrow portion (liquid passage 11) of the pipette tip P, the magnetic particles 2 can be collected sufficiently with a small number of arresting operations. Normally, the number of arresting operations is set to 1 or 2.

In this kind of pre-processing a method is available whereby the amounts of parent samples are made constant before processing. Because this apparatus processes a set of four samples simultaneously, a difference in the amount among parent samples, i.e., a difference in liquid level, poses a problem.

When the amounts of parent samples are not equal, the apparatus may check the amounts of the parent samples prior to the processing and thereby decide an appropriate position to which the distribution unit 29 needs to be lowered during the distribution operation.

As for the measuring of liquid levels, let us take an example where four samples are inspected at the same time and the distributor having four ganged pipette tips P attached to the nozzles N is used. A pressure sensor is provided only to one of the four ganged nozzles N.

First, a pipette tip P mounted to the nozzle N provided with a pressure sensor is inserted into a container in which a first sample is stored. After the liquid level is measured, the pipette tip P is removed and put on the storage area. Next, the nozzle N having the pressure sensor is attached with a new pipette tip P for another sample, which is then inserted into a container that holds a second sample. While measuring the liquid level, the pipette tip P draws in the second sample so that the liquid level is equal to the level of the first sample. These operations are repeated for four samples to make the liquid levels of the four samples equal, allowing the four samples to be processed simultaneously.

When liquid or reagent is distributed, if the front end of the pipette tip P is inserted deep into the liquid, a significant amount of liquid adheres to the outer wall of the pipette tip P, which may affect the measuring precision. To address this problem, the liquid level is continuously checked by the liquid level sensor while performing processing.

Another use of the pressure sensor is measurement of reagents in the reagent containers placed on the reagent unit 23. These reagent containers are supplied with a predetermined amount of a specified reagent beforehand. When the amount of reagent is not sufficient, the processing is likely to be interrupted. To prevent this, a check is made to see if the amount of reagent is sufficient before starting the processing. If the reagent amount is found insufficient, an alarm may be issued to prompt the operator to replenish the reagent.

Further, the liquid level sensor can detect clogging during suction. During the measurement of a normal liquid level, the load of suction is small. When the suction load is higher than a predetermined value, this is taken as a sign of difficulty in performing suction, i.e., clogging. Such clogging may also occur when the viscosity of the sample itself is high. When the liquid sensor detects the clogging, the controller 34 issues a predetermined alarm on the screen to alert the operator to take a necessary action, such as removing the sample in question.

Figure 12:
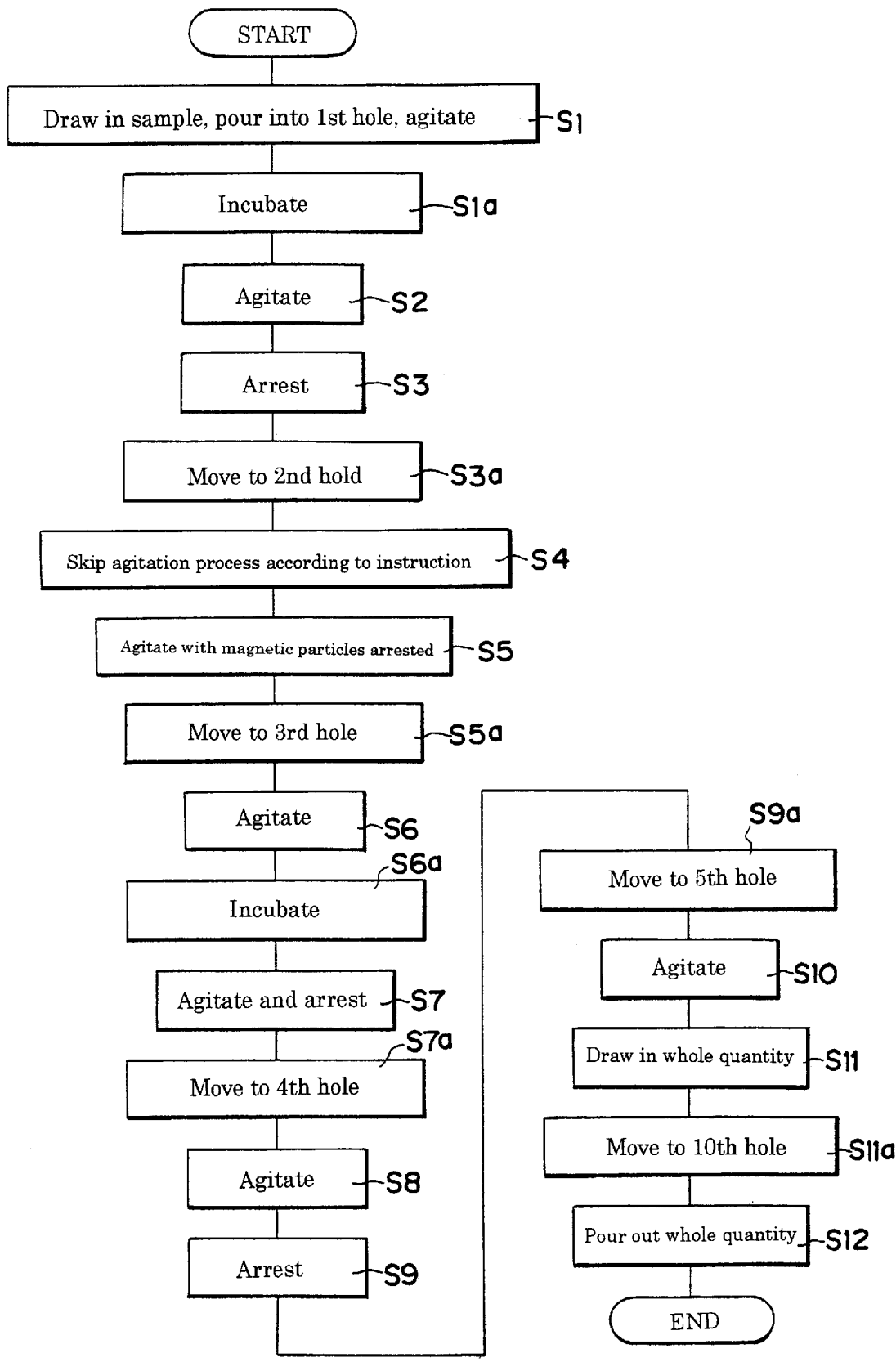
FIG. 12 is a process flow diagram according the first embodiment.

Next, the process steps for performing an immunochemical assay by means of a chemical luminescence method are explained by referring to the instructions shown in FIG. 12. This process steps are carried out based on the registered procedure and times according to the instructions from the controller 34.

The data corresponding to the processing shown in FIG. 11 are entered on the work sheet, which is read by the automatic input unit 47 to provide desired settings.

Then, the specified content analyzing unit 482 checks the work sheet to find that there are a plurality of samples and that processing consists of twelve steps S1 to S12, and then the unit 482 assesses data, such as the contents of each process, the kinds, amounts and positions of reagents, the amounts and positions of samples, the incubation times, the presence or absence of request for arresting magnetic particles, the number of agitation operations, the number of reactions, and the presence or absence of request for pre-processing and for mid-processing.

The numbers S1 to S12 assigned to the process steps agree with the numbers representing the sequence of processes in FIG. 11.

In this embodiment, specified holes in the container cartridge 25 are supplied, prior to the processing, with a predetermined amount of a reactive insoluble magnetic substance suspended liquid, a predetermined amount of a cleaning liquid and a predetermined amount of a marker liquid 6. The measuring hole of the measuring cell unit 26 is supplied with a substrate liquid 7 to enable the luminescent state to be measured. Thus, no pre-processing or mid-processing is specified.

Then, the processing pattern decision unit 483 sets the net processing times A, B, C based on the result of data assessment, and determines and specifies the processing pattern to the SEQ control specifying unit 481.

When the processing is initiated, step S1 starts a sample SEQ program 48a which causes the controller 34 to move the distribution unit 29 and stage 32 to where the tip rack 22 is located. Then, the distribution unit 29 is lowered to mount the pipette tips P to the four ganged nozzles N. The pipette tips P draw in a predetermined amount of reagent from the reagent unit 23 and is moved to the container cartridge 25, to which a predetermined amount of reagent is distributed.

The positioning of the pipette tips P is achieved by forward and backward movement of the stage 32 and lateral movement of the distribution unit 29. The distribution unit 29 moves the four ganged nozzles N in parallel and simultaneously.

Then, with the distribution unit 29 and/or the stage 32 moved a specified distance, an appropriate pipette tip P draws in a required amount of a first sample from a specified sample container of the sample container unit 27 and pours it into a specified hole of the container cartridge 25 in a rough amount.

Next, the preliminarily distributed sample is drawn into the pipette tip P and measured to an exact predetermined quantity. The pipette tip P containing the exact predetermined amount of the first sample is transferred to the first hole containing a reactive insoluble magnetic substance suspended liquid, into which the pipette tip P pours the whole amount of the sample liquid. The mixture of the first sample and the reactive insoluble magnetic substance suspended liquid is repetitively drawn into and discharged from the pipette tip P (a pumping operation) to produce a uniformly mixed state of the magnetic particles 2.

When the processing of one container cartridge 25 (four samples) reaches a specified stage, the incubation time of the first sample is used at step S1a to move the distribution unit 29 and the stage 32 to the processing of a second sample in another container cartridge 25 and the similar processing is performed. In this way, different samples are processed so that the uses of the distribution unit 29 do not overlap.

Figure 13A:
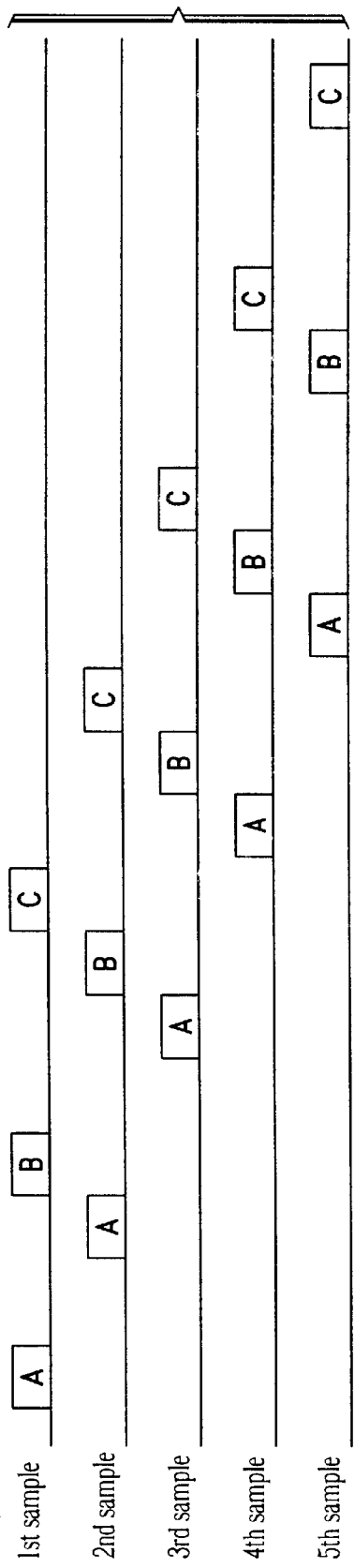
FIG. 13 is a time chart when a plurality of samples are processed simultaneously.
Figure 13B:
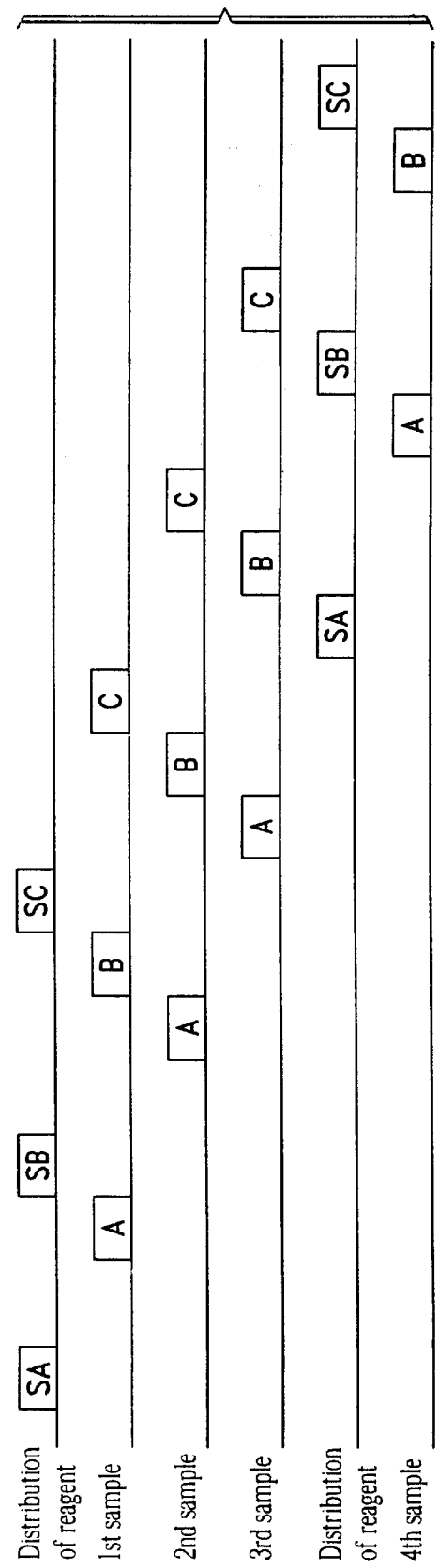

FIG. 13(a) shows a time chart for the processing of a plurality of samples using the two-step method (in which two reactions are performed) in a case where the interval between A and B of the first sample corresponds to the first incubation time, during which the processing A of the second sample is performed.

At step S2, in the first incubation time after the processing A of the second sample is ended, the distribution unit 29 is returned to the processing of the first set of liquids of the first sample, where the agitation SEQ program is started to cause the pipette tips P stored in the tip rack 22 to be attached to the nozzles and to rapidly repeat the suction and discharge operation on the incubated mixture liquids held in the container cartridge 25 for thorough mixing.

After mixing, the arrest SEQ program is started at step S3 to arrest the magnetic particles 2. In arresting the magnetic particles, the magnetic mechanism shown in FIG. 5 moves the magnet M, which attracts the reactive insoluble magnetic substance, toward and away from the outer surface of the liquid passage 11 of the pipette tip P.

At this time, the magnetic particles 2 suspended in the mixture liquid drawn into the pipette tip P at a low speed are attracted to the inner sidewall of the liquid passage 11 by the force of the magnet M placed on the outer side of the pipette tip P as they move past the separation region 11a of the pipette tip P. The suction height of the mixture liquid is such that when the whole mixture liquid is drawn in, the bottom level is equal to the lower end of the magnet M to ensure that the magnetic particles 2 taken into the pipette tip P can be completely arrested.

After the magnetic particles 2 are arrested in this manner, the mixture liquid except for the magnetic particles 2 is discharged into the first hole of the container cartridge 25 and drained out, with only the magnetic particles 2 remaining in the pipette tip P.

At step S3a, the pipette tip P with the magnetic particles 2 is moved to the second hole.

Because the "arrest" item is flagged as shown in FIG. 11, step S4 omits the agitation operation and moves to step 5.

At step S5, the pipette tip P draws in a cleaning liquid from the second hole. At this time, the magnet M is put close to the outer sidewall of the liquid passage 11 of the pipette tip P having the separation region 11a and the cleaning liquid is pumped at high speed two or more times to clean the whole magnetic particles 2 efficiently.

After the pumping is finished, the pipette tip P slowly draws in a predetermined amount of the cleaning liquid from the hole. At this time, the magnet M is brought close to the pipette tip P again to arrest all the magnetic particles 2 floating in the cleaning liquid drawn in. The cleaning liquid excluding the magnetic particles 2 are discharged into the hole, with only the magnetic particles 2 remaining in the pipette tip P.

At step S5a, the pipette tip P with the magnetic particles 2 is transferred to the third hole. At step S6, the pipette tip P draws in a marker liquid. At this time, the magnet M is moved away from the pipette tip P to release the magnetic particles 2. Pumping the marker liquid 6 makes the reaction between the whole magnetic particles 2 and the marker liquid 6 uniform.

Then, the second incubation of the first sample starts.

When the second incubation starts, another container cartridge or the distribution unit 29 is moved to perform the processing A on the third sample, as shown in FIG. 13(a).

Then, when the pumping is finished and the first incubation of the third sample starts, the distribution unit 29 moves to the processing B of the second sample. When the processing B is finished and the second incubation of the second sample starts, the distribution unit 29 moves to the processing C of the first sample.

At step S7, the pipette tip P draws in a predetermined amount of the marker liquid 6 from the hole. At this time, the magnet M is brought close to the pipette tip P to arrest all the magnetic particles 2 suspended in the marker liquid 6 drawn in. Then, the marker liquid 6 excluding the magnetic particles 2 is discharged into the hole, with only the magnetic particles 2 remaining in the pipette tip P. At step S7a, the pipette tip P with the magnetic particles 2 is transferred to the fourth hole, where at step S8 and step S9, it draws in a cleaning liquid and performs cleaning and arresting of the magnetic particles 2 in the same procedure as mentioned above.

At step S9a, the pipette tip P with the cleaned magnetic particles 2 is sent to the fifth hole, where at step S10 it draws in a substrate liquid 7. At this time, the magnet M is moved away from the pipette tip P to release the magnetic particles 2 and the pipette tip P repeats a rapid pumping operation, sucking and discharging the substrate liquid 7 at high speed, to make the reaction between the whole magnetic particles 2 and the substrate liquid 7 uniform.

Then at step S11, the pipette tip P draws in the whole liquid including the substrate liquid 7 and, at step S11a, moves to the tenth hole, into which it delivers the whole liquid at step S12, thus completing the processing on the first sample.

When the above pumping is finished, the pipette tip P is again transferred to the pipette tip unit 24 where it is stored.

With the above processing on the first sample completed, the processing A of the fourth sample is started and the similar procedure to the above is repeated according to FIG. 13(a).

The processed liquid is moved to a measuring cell of the measuring cell unit 26. With elapse of a predetermined time, the stage 32 is moved to transfer the measuring cell to the measuring position in the optical measuring unit 28.

At this measuring position, the amount of luminescence of the processed liquid is measured by an optical measuring device that is compatible with a specified measuring method. Now, a complete sequence of processing is ended.

If a mid-processing is requested, the processing pattern decision unit 483 determines the processing pattern so that reagents can be supplied in idle times between the processing, i.e., in the reagent supply times SA, SB, SC shown on the display screen 41a. The SEQ control specifying unit 481 gives the corresponding instructions to the distribution unit and the container feeding device.

The mid-processing can prevent drying, contamination or degradation of reagents, which would result when the reagents are supplied beforehand, and can perform efficient and reliable processing by supplying required reagents immediately before the associated processing is initiated.

Although this embodiment has employed a four-nozzle assembly in the distribution unit 29, the unit may have eight or any other number of nozzles or even a single nozzle, all requiring only the same operation procedure. The number of ganged nozzles can be changed according to the capacity of the equipment.

Second Embodiment

Figure 14A:
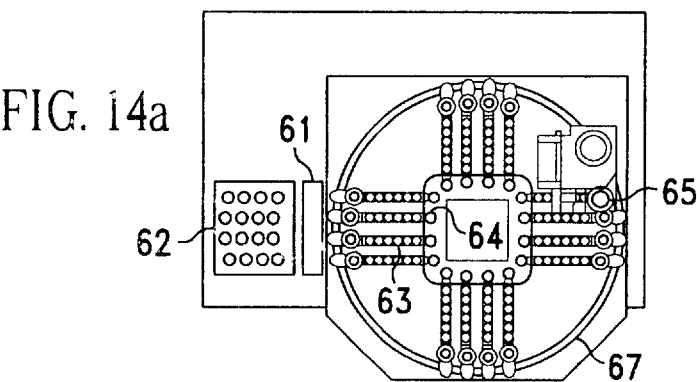
FIGS. 14a–14c is a schematic view showing a configuration of the apparatus as the second embodiment of this invention.
Figure 14B:
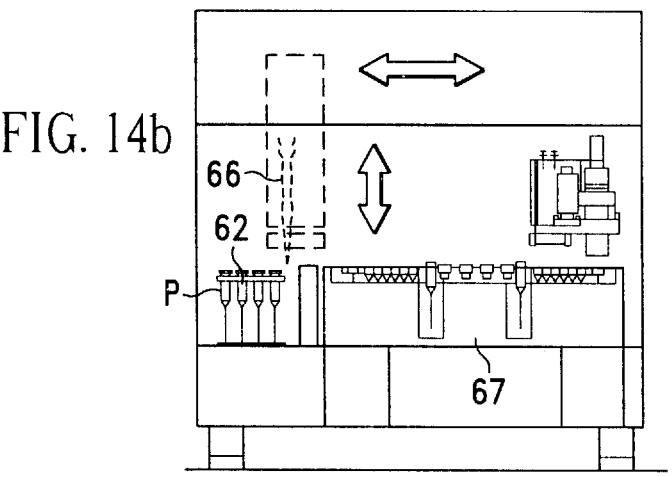
Figure 14C:
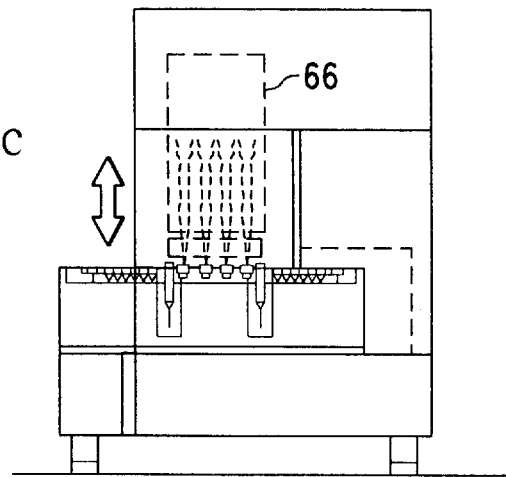

The apparatus of this embodiment, as shown in FIG. 14, includes a rotary stage 67 for moving a mounted container cartridge 63 to a specified position; and a distribution unit 66 and an optical measuring unit 65, both provided over the rotary stage 67. The distribution unit 66 is moved in the diametrical direction of the stage and attached with pipette tips P for performing various works. The optical measuring unit 65 has a PMT that moves up or down and counts photons by enclosing a sample and shielding external light.

The distribution unit 66 is provided integrally with a magnet movement control unit that brings the magnet toward and away from the pipette tip P. The distribution unit 66 has four ganged nozzles and can perform a B/F separation (separation between bound antigen-antibody complexes and free antibodies) and agitation and cleaning of magnetic particles by pumping (repetitive suction and discharge operations).

The apparatus also includes a tip rack 62 that holds new pipette tips P to be mounted to the nozzles of the distribution unit 66 for supplying and dividing sample liquids; and a discard unit 61 into which spent pipette tips P are thrown away.

The rotary stage 67 is rotated to transfer a plurality of radially mounted container cartridges 63 to desired positions according to instructions.

Figure 15:
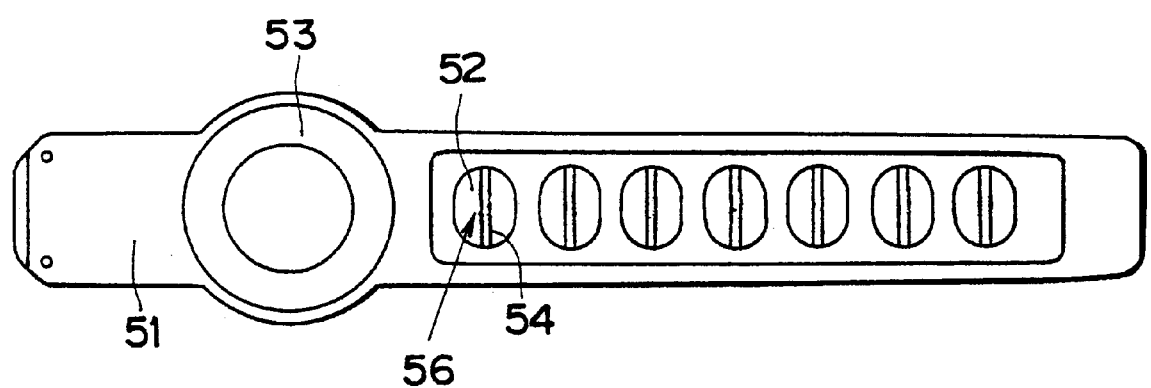
FIG. 15 is a schematic diagram showing a container cartridge.

As shown in FIG. 15, container cartridge 63 of this embodiment has a base portion 51 made of a transparent material such as glass and plastics which is formed with, for example, eight holes.

Of the eight holes, the one formed at one end is an optical measuring hole 53. The arrangement and number of these holes can be determined according to the reaction steps. The other seven holes 52 have their bottoms V-shaped in cross section. On the inner surface of the bottom 56 of each hole 52 a groove 54, U-shaped in cross section, is formed along the inclined inner surface.

This groove 54 is formed narrower than the diameter of the front end portion of the pipette tip P, so that when the front end portion of the pipette tip P contacts the inner bottom portion of the hole 52, the whole sample contained in the hole 52 can be drawn in through the groove 54, thus enabling the exact predetermined amount to be extracted.

Four container cartridges 63 are arranged in parallel and directed toward the center of the rotary stage 67 in such a way that the measuring holes 53 will align with the position of the optical measuring unit 65.

With the container cartridges 63 arranged in this manner, the position of the optical measuring unit 65 remains unchanged when viewed from the measuring hole 53, so that there is no need to move the optical measuring unit 65. The four ganged nozzles of the distribution unit 66 are also laid out according to the arrangement of the container cartridges 63. It is conceivable to arrange the container cartridges 63 in a line (which corresponds to a tangential line of the rotary stage). In that case, the optical measuring unit 65 needs to be moved between two positions-the measuring holes 53 of the central two container cartridges 63 and the measuring holes 53 of the outer two container cartridges 63.

In this apparatus, one set of four container cartridges 63 is supplied with reagents, cleaning liquids and samples beforehand and then set in position on the stage before undergoing processing. The basic sequence of process steps for this apparatus is similar to that of the first embodiment, except that when the processing moves from one set to another, the rotary stage 67 needs to be rotated.

Third Embodiment

Figure 16A:
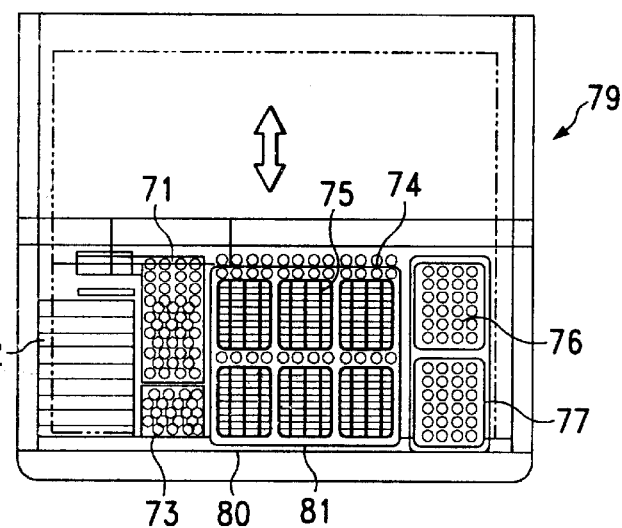
FIGS. 16a–16c is a schematic view showing a configuration of the apparatus as the third embodiment of this invention.
Figure 16B:
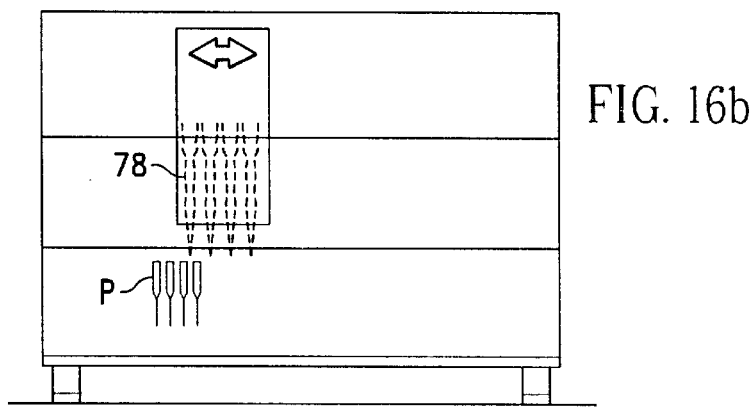
Figure 16C:
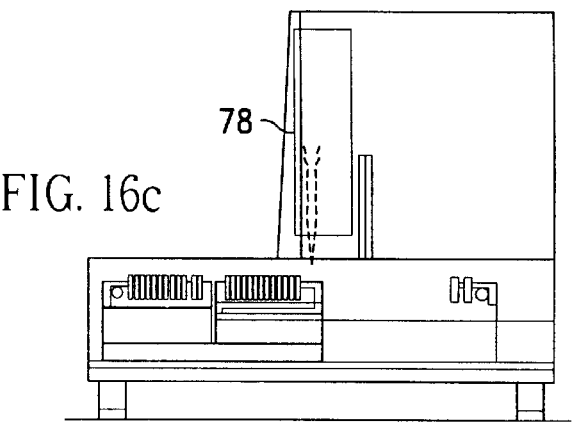

FIG. 16 shows a system unit 79, which incorporates a controller as in the first embodiment. The controller receives a variety of kinds of instructions from a keyboard (not shown) and a display device (not shown) displays necessary information.

The system unit 79 has a stage 80 mounting a variety of containers and movable longitudinally with respect to the system unit; and a distribution unit 78 provided above the stage 80 and moved laterally and vertically with respect to the system unit. This system unit 79 is not provided with an optical measuring unit (PMI). Hence, measurement is taken by using a measuring device.

The construction of the distribution unit 78 is similar to the above embodiment and its detailed explanation is not given here.

On the stage 80 are provided a reagent unit 72 in which a plurality of reagent containers having a rectangular opening are arranged; a container plate 81 mounting six sets of four container cartridges 75, each container cartridge having a plurality of holes; a tip rack 71; an amplification tip rack 73; and a sample container unit 74 that accommodates samples from each column of the container cartridges 75.

The stage 80 is also provided with temperature-adjusting containers 76, 77. The temperature-adjusting container 76 has its top surface formed with a plurality of container holes for accommodating liquid. Inside the temperature-adjusting container 76 there is a heat block or heat panel to keep the upper container holes at a constant temperature (for instance 60(C). The other temperature-adjusting container 77 has a Peltier device inside which has a heat absorbing capability and is used as a cooling container.

A heat block is also provided under the container plate 81 to keep the container cartridges 75 on the container plate at a constant temperature. Because this system unit has the temperature-adjusting container 77, it can control the temperature easily and cope with a plurality of temperature conditions quickly. The basic sequence of processing performed by this system unit is similar to the first embodiment.

Fourth Embodiment

Figure 17A:
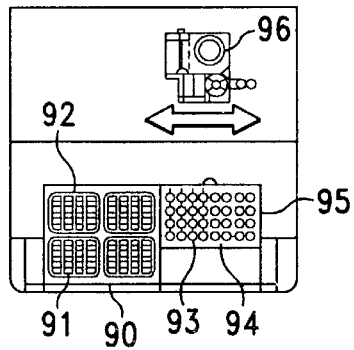
Figure 17B:
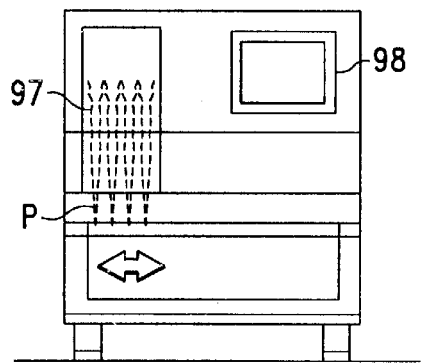
Figure 17C:
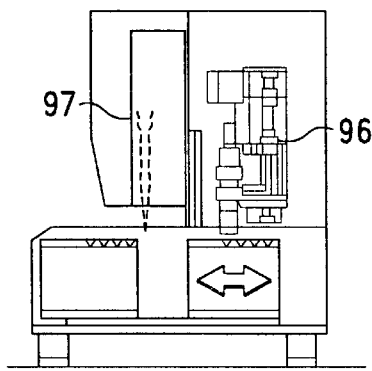

FIG. 17 shows the fourth embodiment of this invention, which incorporates a controller as in the first embodiment. Instructions for this controller are entered from a touch keyboard provided on a monitor unit 98, which displays information on a liquid crystal display.

The system unit 99 has a stage 90 mounting various containers and movable longitudinally with respect to the system unit; a distribution unit provided above the stage 90 and movable laterally and vertically with respect to the system unit; and an optical measuring unit (PMT) 96.

The distribution unit 97 and the optical measuring unit 96 are similar in construction to the first embodiment and their explanations are omitted here.

On the stage 90 there are arranged a container plate 92 and a container case 95. The container plate 92 has mounted thereon four sets of four container cartridges 91, each container cartridge having a plurality of holes.

To the holes of the container cartridge 91 are injected beforehand a required reagent and a cleaning liquid. The sample hole is injected with a sample liquid. The container cartridges 91 are transported sealed entirely and, upon being set in this system unit, can immediately start to be processed.

Figure 18:
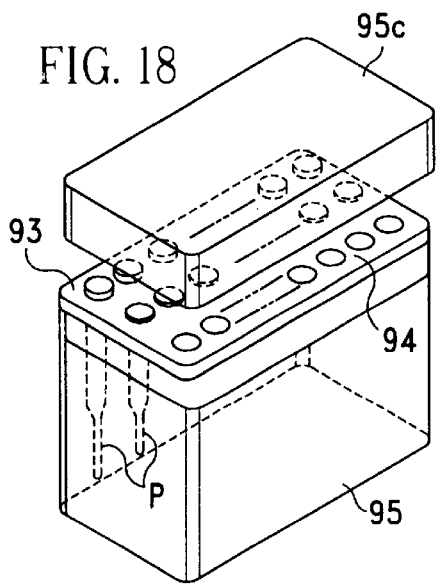
FIG. 18 is a perspective view showing a case accommodating the container of the fourth embodiment.
Figure 18A:
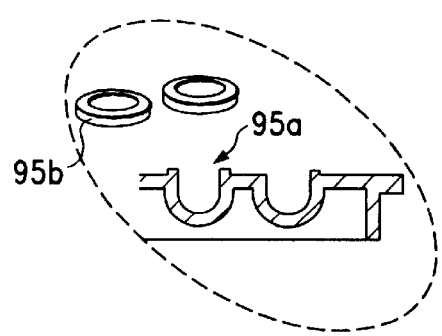

The container case 95, as shown in FIG. 18, is made of paper and molded at the top surface, about half of which is provided with a tip accommodating unit 93 for accommodating pipette tips P. The other half of the top surface is provided with a measuring container unit 94 which is formed with a plurality of holes 95a for accommodating liquid to be measured. Each of the holes 95a can be attached with a cap 95b. The container case has a partition plate therein to isolate the pipette tips P from one another. This container case is disposed of after use and therefore is simple in management. The container case allows the use of a cover 95c at the top, which facilitates transport and storage.

Fifth Embodiment

By referring to FIGS. 19 to 22, the basic control system of the apparatus 100 of this embodiment is explained. The control system of the apparatus of this embodiment controls the liquid distribution, reaction, incubation, agitation, cleaning and measurement.

Figure 19:
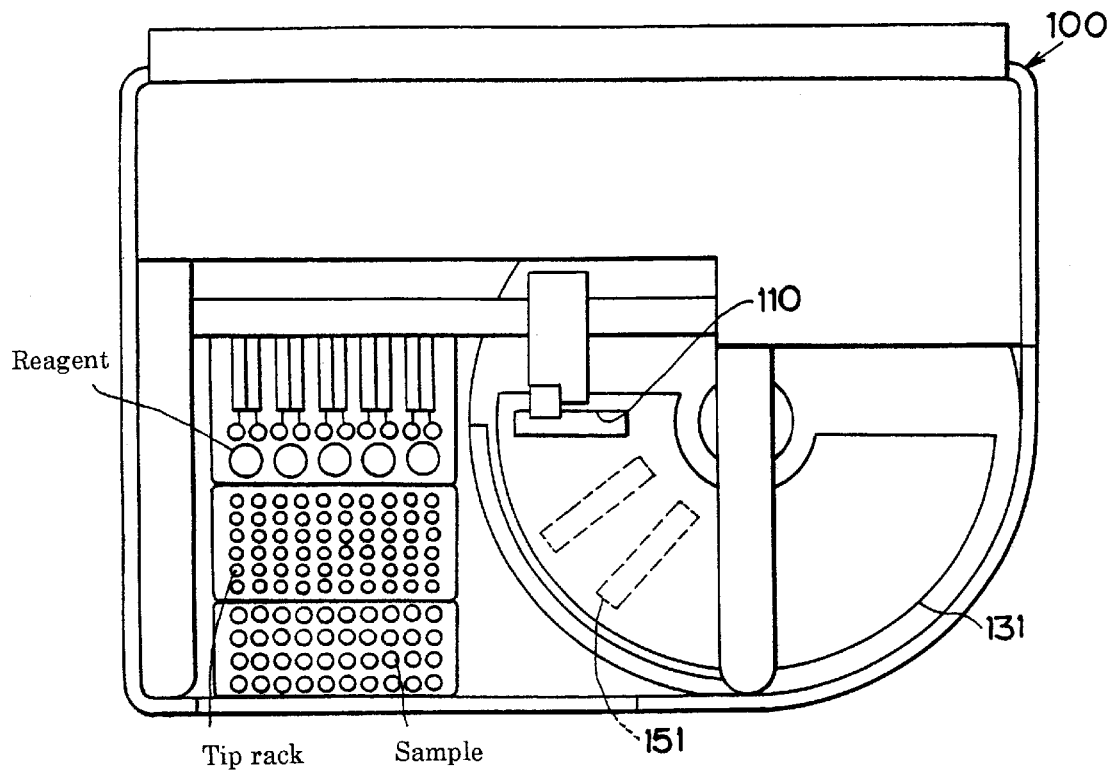
FIG. 19 is a plan view of the apparatus as the fifth embodiment of this invention.
Figure 20:
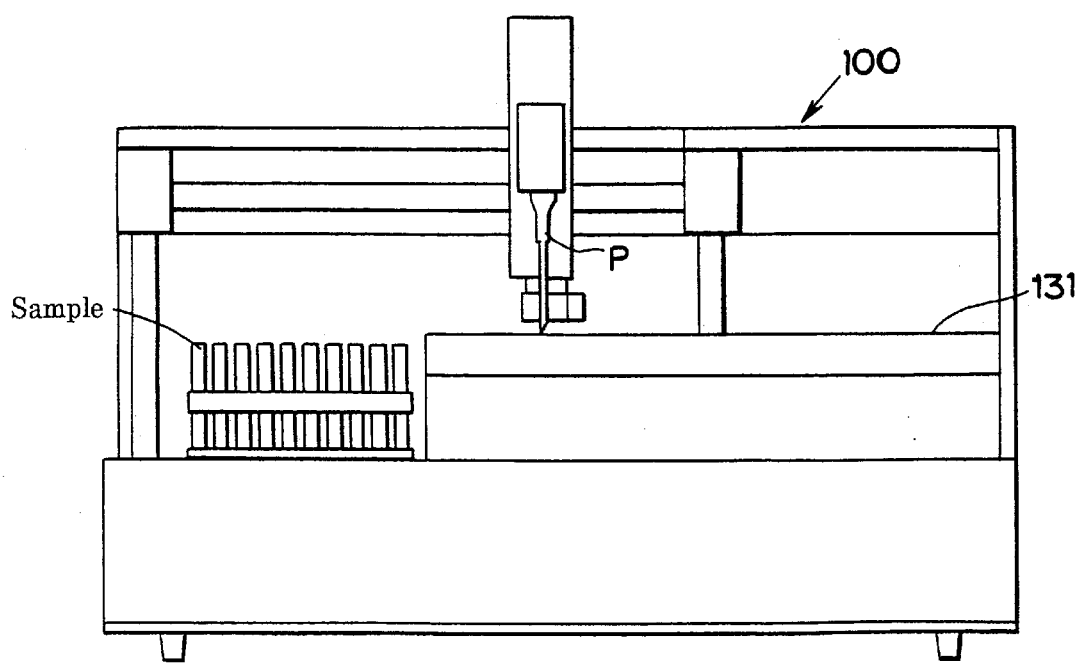
FIG. 20 is a front view of the apparatus as the fifth embodiment of this invention.
Figure 21:
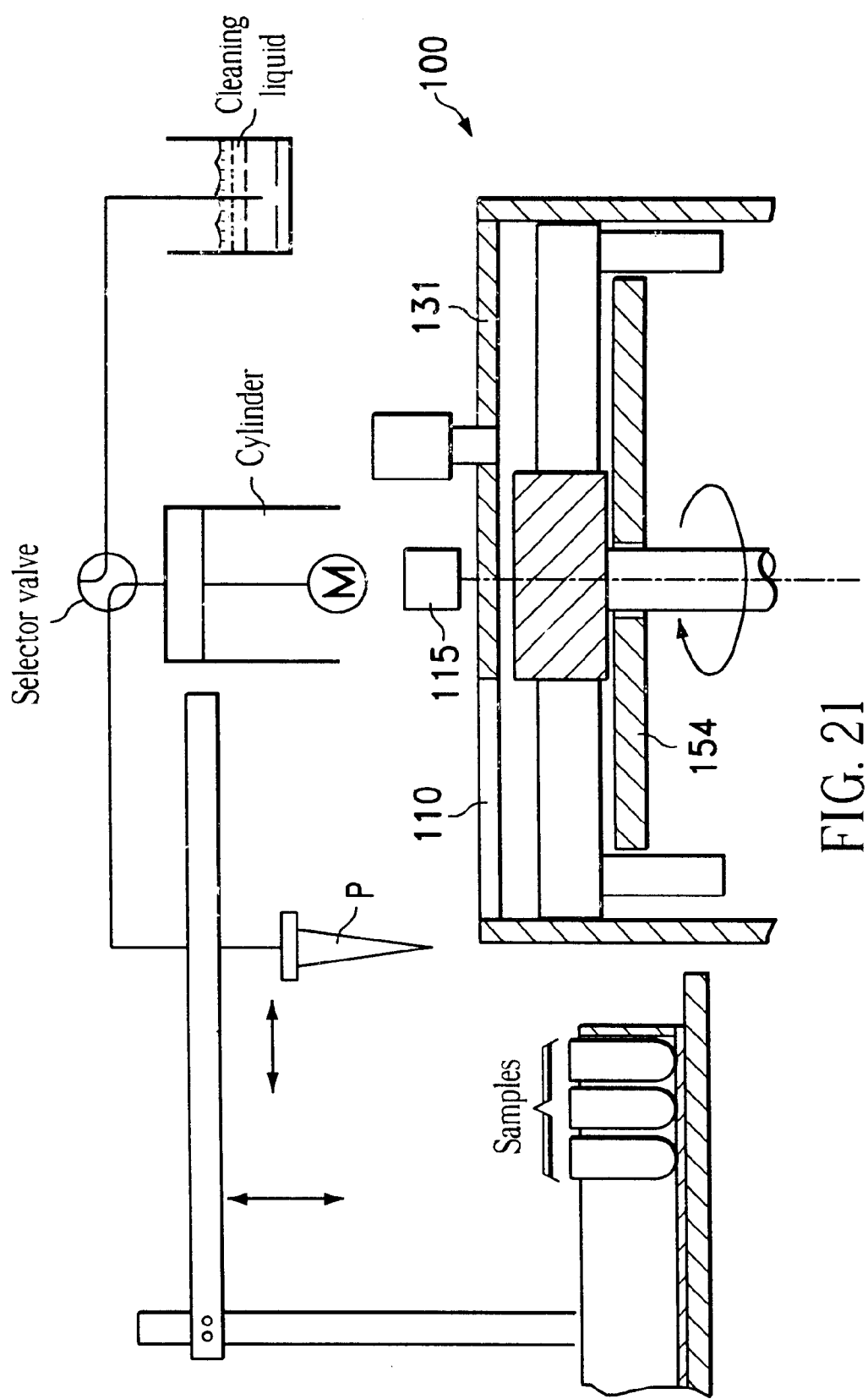
FIG. 21 is a schematic diagram showing the outline configuration of the apparatus of the fifth embodiment.

As shown in FIGS. 19 to 21, the apparatus of this embodiment includes a CPU and memory 140 that performs various control on the apparatus 100; a display unit 141 that displays instructions for loading the container cartridges 151 and the results of analyses; and a bar code read control unit 166 that corresponds to the container cartridge information reading means and which reads and decodes by a bar code reader 115 bar codes attached to that end of the container cartridge 151 loaded in the rotary stage 131 which is closer to the center of the rotary stage 131.

Figure 22:
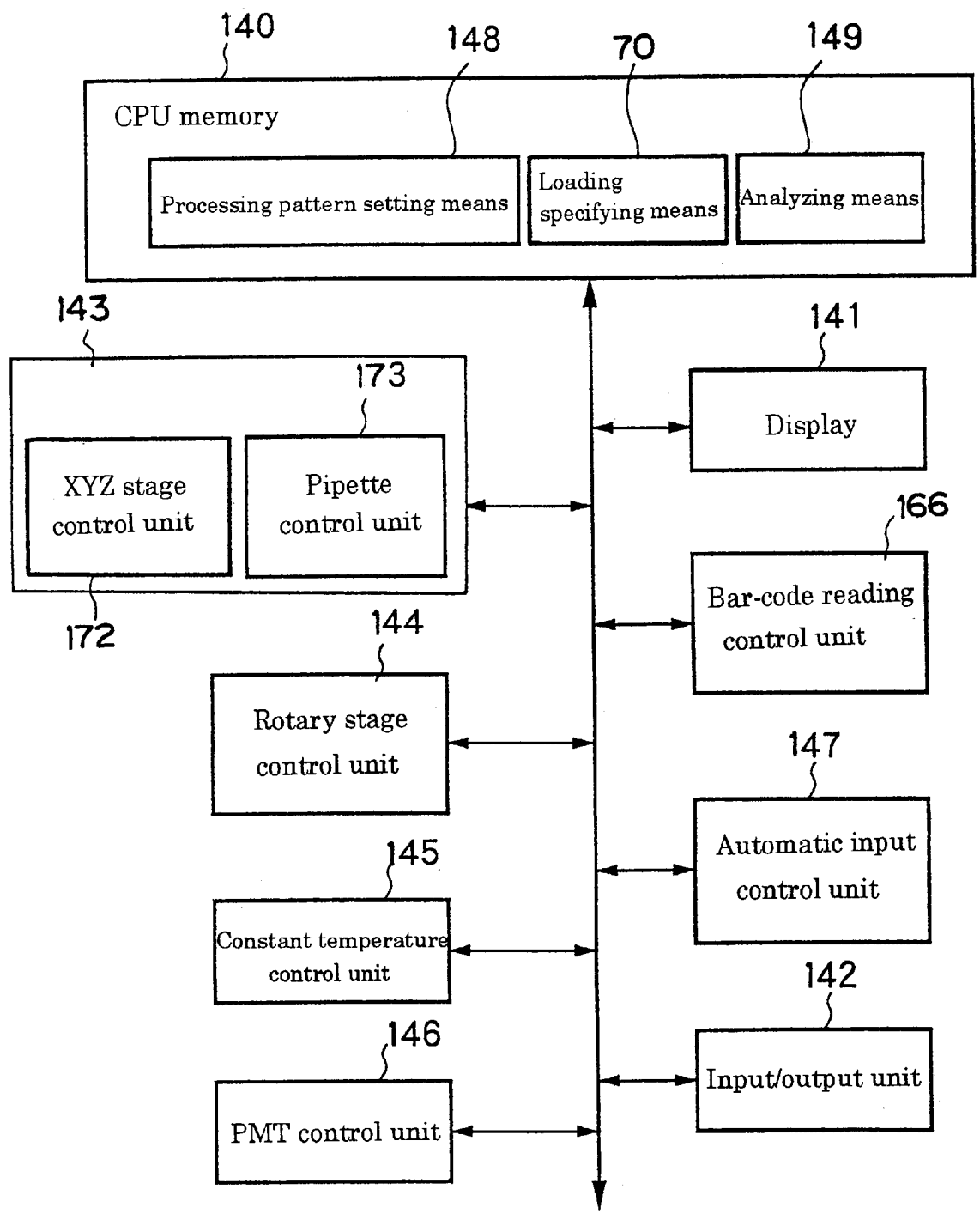
FIG. 22 is a block diagram showing the control system of the fifth embodiment apparatus.

The apparatus also includes an automatic input control unit 147 which corresponds to an item specification means for specifying items that can undergo a series of processing using the same container cartridge and which controls automatic input of sample item information as by optical mark reader (OMR), floppy disk, CDROM and communication; an input/output unit 142 having a keyboard and mouse for entering associated information and a printer for producing recorded outputs; a pipette device control unit 143 for controlling the pipette device; a rotary stage control unit 144 for controlling the rotary stage 131; a constant temperature control unit 145 for controlling at a constant temperature a thermostatic oven or heater provided to the fixing plate 154 of the rotary state 131; and a PMT control unit 146 for controlling the PMT. In FIG. 22, reference number 172 represents an XYZ stage control unit for controlling the movement of the distribution unit; reference number 173 denotes a pipette control unit for controlling the action of the pipette.

The CPU and memory 140 includes a processing pattern setting means 148, a cartridge loading specifying means 170, and an analyzing means 149. The processing pattern setting means 148 sets by program a processing pattern for each process according to the number of cleaning processes contained in each item entered through the automatic input unit 147, the number of specified items, the processing time of each item, the processing time of each process included in each item or the container cartridge position. The cartridge loading specifying means 170 urges the user to load those container cartridges 151 which have identifier information associated with the item onto the rotary stage 131. The analyzing means 149 analyzes the result obtained through the PMT control unit 146.

In the memory is already stored a program that displays the contents of each item and the procedures for processing each of the items. The CPU and memory 140 of course contains other various control instructions associated with this apparatus.

The operation of this embodiment is explained. The operator writes items representing inspections to be performed on the mark sheet in the form that can be read by the optical mark reader which corresponds to the item specifying means. Other data to be written into the mark sheet include registration numbers of patients. These written information is read by the optical mark reader. The mark sheet filling is done by marking desired items representing inspections to be performed or by marking the number of corresponding items.

The reading operation is controlled by the automatic input control unit 147. The cartridge loading specifying means 170 in the CPU and memory 140 requests that the container cartridges 151 corresponding to the specified item be loaded into the rotary stage 131. This request is made by displaying on the screen of the display unit 141 the total number of container cartridges for the specified items to be loaded.

The operator, based on the information displayed on the screen, loads the specified number of container cartridges 151 for the items, one by one, into the insertion opening 110 of the rotary stage 131.

In this way, the container cartridges corresponding to each item are loaded randomly into the rotary stage 131.

With the required number of container cartridges 151 loaded into the rotary stage 131, the CPU and memory 140 causes the rotary stage 131 to make one turn to allow the bar code reader 115 to read the bar code marked at one end, near the center, of each container cartridge 151.

The processing pattern setting means 148 in the CPU and memory 140 recognizes the quantities and positions of each item according to the bar code marked on each container cartridge 151.

Based on the result of recognition, the processing pattern indicating the order in which the items are processed is set as follows.

The processing pattern is so set as to perform as many processing in as short a time as possible, i.e., to improve processing efficiency. On top of that, the operations of the rotary stage 131 needs to be made as small as possible.

If the pipette device is made to devote itself to the processing of one item until the processing of one container cartridge is finished, by pegging the container cartridge at the distribution position, the processing time for all items, which is equal to the processing time for each item multiplied by the number of items, will become intolerably large.

Most of the processing time, however, is spent for incubation (constant temperature reaction), during which time the pipette tips P are idle. Hence, using this idle time for performing other processing can reduce the overall processing time.

For this purpose, as described in the preceding embodiment, the same process step is repeated for different samples so that the same program can be used eliminating the need to read out different programs repetitively and minimizing the operations of the pipette tips.

In this embodiment, too, the items are classed and a group of same or similar items are subjected to the same processing.

The same process step in a group of same or similar items is performed on a plurality of container cartridges. After this processing is complete, the operation moves to the next process step. This operation arrangement allows the pipette tips to perform, while each container cartridge is incubated, the same process step on the number of container cartridges that can be processed within the incubation time, improving the processing efficiency.

This invention fully utilizes the non-processing time Iji of the pipette tip, such as an incubation time in a process step I for an item j, i.e., a time in which the pipette tip cannot perform subsequent processing one after another on the same container cartridge.

The processing is controlled such that the following relation holds.

$$P \times n^j_i + R^j_i \leq I^j_i$$

where $n^j_i$ represents the number of container cartridges that can be processed by the pipette tips in the non-processing time $I^j_i$, P represents a maximum time taken by the pipette tip for processing such as sample distribution (very short compared with the incubation time), and $R^j_i$ represents a total time in the non-processing time $I^j_i$ required for container cartridge transfer that elapses from the moment a container cartridge is fed for processing to the moment the same container cartridge returns to the home position for sample distribution.

Hence, at least $n^j_i$ items, determined from the above formula, can be processed in parallel (including the item originally intended to be processed during this time). In that case, the transfer of container cartridges is performed by rotating the rotary stage 131 in the forward direction to further reduce the time of $R^j_i$.

If a series of processing is performed successively on each cartridge, the non-processing time of the pipette tip cannot be utilized, requiring a huge amount of time for processing all container cartridges which is expressed by $\Sigma^{ij} n^j_i \cdot I^j_i$ (summing for i and j).

Considering the above, the processing pattern setting means 148 of this embodiment sets the processing pattern as follows.

First, for the items that were set, this means 148 reads data representing the contents of these items stored beforehand in memory.

Next, it checks the number of cleaning process steps included in the processing of each item.

The items are classed according to the number of cleaning process steps they contain. The difference in the number of cleaning process steps determines the fundamental processing for each item, such as the number of distribution process steps performed in individual items and the processing time taken by the items. The items having the equal number of cleaning process steps are similar in processing.

The items that were classed into groups according to the number of cleaning process steps are now counted in each group.

Next, the processing pattern setting means 148 checks the incubation process (time) to class the items according to the incubation time and set a processing pattern.

It is assumed, for example, that the items that have one cleaning process step are A, D and E, that items with two cleaning process steps are B and C, and that items with three cleaning process steps are F and G.

The difference among the items included in the same process-step group results from the difference in the kind of reagents and marker chemicals used. Further, for each process-step group, the number of samples in each item are counted. For example, let us assume that in the one-process-step group, the processing item A includes 15 samples, processing item D 11 samples, and item E 14 samples.

Further, the samples are classed according to the incubation time, i.e., time taken by the processing of each item. Suppose the item A takes 20 minutes, item D 32 minutes and item E 20 minutes. The item A and the item E take 20 minutes and are classed in the same group, and the item D which takes 32 minutes is classed as another group.

The difference in the processing time that occurs even when the number of cleaning process steps is equal and the same marker chemical is used occurs because there may be a need to carry out processing with incubation times differentiated.

In that case, when the number of cleaning process steps is one, the number of container cartridges that are processed during one rotation of the rotary stage 131 is preferably set at five cartridges per 30 minutes for efficient processing; when the number of cleaning process steps is two, it is desirably set at four cartridges per 30 minutes for efficient processing; when the number of cleaning process steps is three, it is preferably set at three cartridges per 30 minutes for efficient processing. The above setting is explained below.

When the number of cleaning process steps is one, the processing pattern setting means 148 makes setting so that three processings are performed on the item A, five samples at each processing, that two processings are performed on the item E, five samples at each processing, and that two processings are performed on the item D, five samples at each processing.

As a result, as to the item E, four samples remain unprocessed; as to item D, one sample remains unprocessed.

Similarly, the processing pattern setting means 148 moves to the setting for the processing having two cleaning process steps, and then further to the processing with three cleaning process steps.

After the above batch processing is finished, the processing pattern setting means makes setting so that, as for the one cleaning process step, the remaining four samples of item E and one sample of item D are now processed.

In this way, the processing pattern setting means 148 sets the most efficient processing pattern for the specified items and, according to the processing pattern thus set, specifies control to the rotary stage control unit 144, the pipette tip control unit 143, the PMT control unit 146 and the constant temperature control unit 145, with the system unit 100 executing the operations such as separation, agitation and cleaning efficiently according to the specified control.

Industrial Applicability of the Invention

The preferred fields of application of this invention with the above construction include reactions occurring between a liquid containing magnetic particles and a liquid not containing magnetic particles, and physical and chemical arresting of substances and magnetic particles present in a liquid. Among example substances to be arrested are immunological substances, biological substances and molecular biological substances, such as antigens, antibodies, proteins, enzymes, DNAs, vector DNAs, RNAs, m-RNAs and plasmids. The invention is also applicable for inspection methods and clinical inspection apparatuses that use marker substances-such as isotopes, enzymes and chemical luminescent, fluorescent luminescent and electrochemical luminescent substances-for qualitative and quantitative assay of the immunological, biological and molecular biological substances. In more detail, the invention can be applied to immunoassays, chemical substance reaction inspections, and extraction, recovery and isolation of DNA.

When this invention is applied, for example, to an immunochemical inspection apparatus, it is desired that the sample containers be formed into a cartridge having a plurality of liquid accommodating portions, that samples and reagents required for reactions and processing be supplied beforehand into respective liquid accommodating portions of the cartridge and that the pipette tip be transferred with the magnetic particles arrested on the inner surface of the liquid passage of the pipette tip by magnetic attraction. In this case, the liquid to be processed is supplied into the liquid accommodating portions beforehand. The liquid may also be supplied only partly or, during the processing, supplied in steps. The sample may be extracted in a specified amount directly from a parent sample container. The container cartridge may have only one liquid accommodating portion, or it may be formed into a microplate with a plurality of columns of liquid accommodating portions. When the cartridge is made in the form of a microplate, the sample distribution unit may be arranged according to the columns of the liquid accommodating portions to provide multiple channels, substantially increasing the processing capacity of the apparatus.

What is claimed is:

1. A computer implemented method of controlling a sample distributor, comprising:

entering specification information for controlling the sample distributor, the specification information including at least one operation condition for specifying:

whether a magnetic particle is attracted to an inner sidewall of a liquid passage of the sample distributor by a magnetic field; and a selection from among: a specification of whether a suction and discharge operation is performed by the sample distributor, a position of the suction and discharge operation, a time of the suction and discharge operation, an order of the suction and discharge operation, a number of times of the suction and discharge operation, a quantity of the suction and discharge operation, and a speed of the suction and discharge operation;

analyzing the specification information;

generating a processing pattern for the sample distributor based upon the analysis of the specification information; and generating instructions for executing the processing pattern.

2. The method of claim 1, wherein the specification information includes at least one of: a material condition and a reaction condition.

3. The method of claim 1, wherein analyzing the specification information comprises determining at least one of:

a number of samples;

a number of divided samples;

a material condition;

a reaction condition;

the operation condition;

whether to perform pre-processing; and whether to perform mid-processing.

4. The method of claim 1, wherein analyzing the specification information comprises identifying data contained in the specification information, and wherein generating the processing pattern comprises:

setting a processing pattern according to the data contained in the specification information.

5. The method of claim 4, wherein the data is selected from the group consisting of:

a number of divided samples, a total process time for each item, a time taken by each process contained in each item, and a container cartridge position.

6. The method of claim 1, wherein when two or more samples are processed by the system, a minimum incubation time $t_{min}$ is set to be larger than a total working time T and an incubation time t to be set is an integer times the minimum incubation time $t_{min}$.

7. The method of claim 6, wherein when two or more samples are processed by the system and mid-processing is specified, the times required by the mid-processing are shorter than each working time based on each working time, into which the total working time T of the entire processing including one or more reaction processes is partitioned by one or more incubations.

8. The method of claim 1, wherein when divided samples are processed by the system, a minimum incubation time $t_{min}$ is set to be larger than a total working time T and an incubation time t to be set is an integer times the minimum incubation time $t_{min}$.

9. The method of claim 8, wherein when divided samples are processed by the system and mid-processing is specified, the times required by the mid-processing are shorter than each working time based on each working time, into which the total working time T of the entire processing including one or more reaction processes is partitioned by one or more incubations.

10. The method of claim 1, wherein generating instructions for executing the processing pattern comprises:

requesting to draw in a required amount of a sample and discharge it into a container accompanying a necessary agitation;

requesting to attract a plurality of magnetic particles bounded to a target substance suspended in a liquid to the inner sidewall by applying the magnetic field; and requesting to agitate by drawing into and discharging from a pipette, and requesting to draw and discharge the liquid in the container.

11. The method of claim 1, further comprising:

passing a liquid containing suspended magnetic particles through a separation region of a pipette portion, the separation region being arranged in the liquid passage connecting a front end portion and a reservoir portion of the pipette portion; and during the passing of the magnetic particle-suspended liquid, applying the magnetic field to the separation region from outside the liquid passage of the pipette portion to attract the magnetic particles to the inner sidewall to separate the magnetic particles from the liquid by translating and rotating the magnetic field into a position proximate the separation region.

12. A system for controlling a sample distributor, comprising:

means for entering specification information for controlling the sample distributor, the specification information including at least one operation condition for specifying:

whether a magnetic particle is attracted to an inner sidewall of a liquid passage of the sample distributor by a magnetic field; and a selection from among: a specification of whether a suction and discharge operation is performed by the sample distributor, a position of the suction and discharge operation, a time of the suction and discharge operation, an order of the suction and discharge operation, a number of times of the suction and discharge operation, a quantity of the suction and discharge operation, and a speed of the suction and discharge operation;

means for analyzing the specification information;

means for generating a processing pattern for the sample distributor based upon the analysis of the specification information;

means for generating instructions for executing the processing pattern; and means for executing the instructions for the processing pattern.

13. The system of claim 12, wherein the means for analyzing comprises:

means for analyzing a sample number;

means for analyzing a sample division;

means for analyzing a reaction content;

means for analyzing a reaction number;

means for analyzing pre-processing; and means for analyzing mid-processing.

14. The system of claim 12, wherein the means for generating a processing pattern comprises:

means for generating a sample sequence control;

means for generating an arrest sequence control;

means for generating an agitation sequence control; and means for generating a whole quantity sequence control.

15. A method of controlling magnetic particles by a sample distributor, comprising:

passing a liquid containing suspended magnetic particles through a separation region of a pipette of the sample distributor, wherein the separation region comprises a liquid passage connecting a front end portion and a reservoir portion of the pipette;

applying a magnetic field to the separation region from outside the liquid passage of the pipette to attract the magnetic particles to an inner sidewall surface of the liquid passage to separate the magnetic particles from the liquid;

entering specification information including at least one operation condition for specifying:
  whether the magnetic particles are attracted to the inner sidewall surface by the magnetic field; and
  a selection from among: a specification of whether a suction and discharge operation is performed by the sample distributor, a position of the suction and discharge operation, a time of the suction and discharge operation, an order of the suction and discharge operation, a number of times of the suction and discharge operation, a quantity of the suction and discharge operation, and a speed of the suction and discharge operation;
analyzing the specification information entered to determine required processing;
determining a processing pattern which the sample distributor follows based on the specification information; and
giving instructions for execution of processing to the sample distributor, or the sample distributor and a container feeding device, according to the determined processing pattern.

16. The method of claim 15, wherein determining the processing pattern comprises:
  based on the specification information, setting the processing pattern so that a suction and discharge speed at which the liquid is drawn into and discharged from the pipette is slow enough to produce a sufficient effect of separation, according to a viscosity of the liquid and a plurality of characteristics of the magnetic particles.

17. The method of claim 15, wherein magnetic particles are arrested in a process comprising:
  drawing in and discharging from the pipette, a mixture of a predetermined amount of a sample and a predetermined amount of a magnetic particle-suspended liquid.

18. The method of claim 17, wherein drawing in the mixture to the pipette comprises;
  maintaining a bottom level of the liquid drawn in at a position equal to or higher than a lower end area of the separation region.

19. The method of claim 17, wherein drawing in and discharging from the pipette comprises;
  keeping a lower end portion of the pipette submerged in a reagent or a cleaning liquid to prevent generation of bubbles due to suction of air.

20. The method of claim 15, further comprising agitating or cleaning the pipette, wherein a percentage of liquid drawn into the pipette from a container can be specified during agitating or cleaning.

21. The method of claim 20, wherein agitating or cleaning comprises:
  sucking air into the pipette.

22. The method of claim 15, wherein the pipette comprises a pipette tip removably attached to one or more nozzles of the sample distributor.

23. The method of claim 15, wherein analyzing the specification information entered to determine required processing comprises:
  checking a number of samples or a number of divided samples;
  checking material conditions, reaction conditions or operation conditions; and
  checking if there is any request calling for pre-processing or mid-processing.

24. The method of claims 15, wherein determining a processing pattern which the sample distributor follows based oh the specification information comprises:
  setting a processing pattern for a sample specified according to data contained in the sample,
  wherein the data includes number of divided samples, a total process time for each sample, a time taken by each process contained in each sample, and a container cartridge position.

25. The method of claim 15, wherein determining a processing pattern which the sample distributor follows based on the specification information,
  wherein two or more samples are used, comprises;
  setting a minimum incubation time $t_{min}$ to be larger than a total working time T; and setting an incubation time t as an integer n times the minimum incubation time $t_{min}$;
  wherein the total working time T comprises one or more reaction processes excluding the incubation time t; and
  wherein the total working time T is entered, measured, or registered.

26. The method of claim 25, wherein the specification information comprises mid-processing,
  wherein determining the processing pattern comprises setting one or more mid-processing times shorter than a working time,
  wherein the working time is partitioned by one or more incubations into the total working time T of the entire processing, and
  wherein the total working time T is entered, measured or registered.

27. The method of claim 15, wherein giving instructions for execution of processing comprises:
  requesting to draw in a required amount of sample and discharge the sample into a container accompanying a necessary agitation;
  requesting to attract the magnetic particles bounded to a target substance suspended in a liquid to the inner sidewall surface by applying the magnetic field;
  requesting to agitate by drawing the liquid into and discharging the liquid from the pipette; and
  requesting to draw and discharge the liquid in the container.

28. The method of claim 15, wherein the specification content analyzing means determines a processing pattern comprising:
  maintaining a liquid suction speed and discharge speed during reaction, agitation and cleaning faster than a liquid suction speed and discharge speed during the magnetic particle separation process.

29. The method of claim 15, wherein the specification content analyzing means determines a processing pattern comprising:
  transferring a plurality of arrested magnetic particles to another position where a target substance bonded to the magnetic particles is subjected to processing,
  wherein the arrested magnetic particles are adhering to the inner sidewall surface.

30. The method of claim 15, wherein the specification information is selected from the group consisting of:
  material conditions, reaction conditions, and operation conditions.

31. The method of claim 30, wherein the material conditions are selected from the group consisting of materials kinds, quantities, accommodated positions and characteristics of a target substance, a sample, and magnetic particles;
  wherein the reaction conditions are selected from the group consisting of number of the reaction, incubation time, and temperature; and wherein the operation conditions include a specification of whether magnetic particles are attached to the inner sidewall by a magnetic field.

32. The method of controlling magnetic particles by a sample distributor according to claim 15, wherein determining a processing pattern which the sample distributor follows based on the specification information comprises:

setting a processing pattern for one or more items that can be respectively processed successively using the same container cartridge, according to a data set for each item;

wherein the data set includes a number of samples, a number of reactions, number of divided samples, a total process time, a time taken by each process contained in each item, and a container cartridge pattern.

33. A control apparatus for controlling magnetic particles by a sample distributor, comprising:

a pipette having a front end portion, a reservoir portion, a liquid passage connecting the front end portion and the reservoir portion, and a separation region in the liquid passage subjected to an action of a magnetic field;

a sample distribution unit for applying a negative or positive pressure to the interior of the pipette to draw or discharge a magnetic substance-suspended liquid into or from the pipette;

a magnetic field source;

a magnetic field source driving device for driving the magnetic field source to apply or remove a magnetic field to or from the separation region from outside the liquid passage;

a control device for controlling the sample distribution unit and the magnetic field source driving device;

a specification information input means for inputting specification information including at least one operation condition for specifying:

whether the magnetic particles are attracted to an inner sidewall of the liquid passage by the magnetic field; and a selection from among: a specification of whether a suction and discharge operation is performed by the sample distributor, a position of the suction and discharge operation, a time of the suction and discharge operation, an order of the suction and discharge operation, a number of times of the suction and discharge operation, a quantity of the suction and discharge operation, and a speed of the suction and discharge operation;

a specification content analyzing means for determining, based on the specification information, a processing pattern that the sample distributor must follow; and a processing pattern execution instructing means for giving instructions for executing the processing to the sample distributor according to the determined processing pattern.

34. The control apparatus of claim 33, further comprising a container feeding device for transferring one or more containers to one or more desired positions, wherein the control device controls the container feeding device, wherein the specification content analyzing means determines the processing pattern that the container feeding device must follow, and wherein the processing pattern execution instructing means gives instructions for executing the processing to the container feeding device according to the determined processing pattern.

35. The control apparatus of claim 33, further comprising an analyzing means for analyzing results generated by the execution of the processing pattern execution instructing means.

36. The control apparatus of claim 33, wherein the pipette further comprises a pipette tip having an opening in the reservoir portion, wherein the opening is removably fitted over a nozzle of the sample distribution unit, and wherein the control device further controls attaching and detaching of the pipette tip to and from the nozzle.

37. The control apparatus of claim 33, wherein the pipette further comprises a path of motion, wherein reagents and cleaning liquids required for quantitative and qualitative assay-and extraction of a magnetic particle-suspended liquid and a target substance are supplied in predetermined amounts along the path; and wherein the pipette is moved along the path to draw and discharge liquids into and from the pipette.

38. The control apparatus of claim 33, further comprising a container with liquid accomodating portions, wherein the portions comprise predetermined amounts of reagents and cleaning liquids required for quantitative and qualitative assay and extraction of a magnetic particle-suspended liquid and a target substance, and wherein the control device moves the container or the liquid accommodating portions to a raised position of the pipette.

39. The control apparatus of claim 33, wherein the container with liquid accomodating portions comprises a plurality of openings, and wherein the openings are covered with a thin film.

40. The control apparatus of claim 33 further comprising pipette tips, wherein the control device controls the pipette tips, and wherein the pipette tips are removably fitted to a plurality of nozzles of the sample distribution unit so that the pipette tips can simultaneously perform separation, agitation and cleaning.

41. The control apparatus of claim 40, further comprising a storage unit for storing the pipette tips.

42. The control apparatus of claim 33, wherein the control device operates in a bottom landing mode, comprising:

the front end portion of the pipette contacts the bottom of a container and is recognized by the control device, the pipette is moved up to a height where the front end portion does not contact the container and, with the front end portion set close to the bottom of the container, the pipette performs a suction and discharge operation.

43. The control apparatus of claim 33, wherein the sample distribution unit has a plurality of nozzles to which a plurality of pipette tips can be removably fitted, and wherein a liquid level sensor for detecting the level of a liquid is incorporated into one of the nozzles.

44. The control apparatus of claim 33, further comprising a container-installed side and wherein a constant temperature device is arranged on the container-installed side.

45. The control apparatus of claim 33, further comprising a reagent bottle side and wherein a constant temperature device is arranged on the reagent bottle side.

46. The control apparatus of claim 33, further comprising a measuring unit comprising a shielding structure and a measuring device for measuring radiation.

47. The control apparatus of claim 46, wherein the measuring unit further comprises a distribution nozzle for supplying a plurality of reagents.

48. The control apparatus of claim 33, wherein the control device performs according to preset information regarding the amount and kind of reagents to use.

49. The control apparatus of claim 33, wherein the specification content analyzing means analyzes each sample to identify data contained in each sample and determines the processing pattern for a sample according to the data contained in each sample.

50. The control apparatus of claim 33, wherein the specification content analyzing means determines the processing pattern comprising:
   a specified content analyzing unit for analyzing contents input by an information input means; and
   a processing pattern decision unit for determining a processing pattern that the distributor should follow.

51. The control apparatus of claim 50, wherein the specification content analyzing unit comprises:
   a sample number/sample division number decision section that checks a number of samples or a number of divided samples from the information input means;
   a processing content and reaction number decision section that checks a sample for material conditions, reaction conditions and operation conditions; and
   a pre-processing/mid-processing decision section that checks the processing pattern for a request calling for pre-processing or mid-processing.

52. The control apparatus of claim 10, wherein the specification content analyzing means determines a processing pattern comprising:
   a means for requesting to draw in a required amount of a sample and discharge the sample into a container accompanying a necessary agitation;
   a means for requesting to attract the magnetic particles bounded to a target substance suspended in a liquid to the inner sidewall by applying the magnetic field;
   a means for requesting to agitate by drawing into and discharging from the pipette; and
   a means for requesting to draw and discharge the liquid in the container.

53. The control apparatus of claim 33, wherein two or more samples are used,
   wherein the specification content analyzing means determines the processing pattern comprising:
   setting a minimum incubation time $t_{min}$ to be larger than a total working time T; and
   setting an incubation time t to be an integer n times the minimum incubation time $t_{min}$.

54. The control apparatus of claim 53, wherein two or more samples are used;
   wherein the specification content analyzing processing pattern determines a processing pattern comprising mid-processing, and
   wherein mid-processing comprises:
      setting the times required by the mid-processing shorter than the working time which is entered, measured or registered, and into which the total working time T is partitioned by one or more incubations.

55. The control apparatus of claim 33, wherein the specification content analyzing means determines a processing pattern comprising:
   setting a suction and discharge speed at which the liquid is drawn into and discharged from the pipette to be slow enough to produce a sufficient effect of separation, when the separation region of the pipette is subjected to a magnetic influence for separation of magnetic particles.

56. The control apparatus of claim 33, wherein the specification content analyzing means determines a processing pattern so that magnetic particles are arrested in a process where a mixture of a predetermined amount of a sample and a predetermined amount of a magnetic particle-suspended liquid is drawn in and discharged in a whole quantity.

57. The control apparatus of claim 56, wherein the specification content analyzing means determines a processing pattern to control a suction drive when the whole quantity of the liquid is drawn in,
   wherein a bottom level of the liquid drawn in is raised at a position equal to or higher than a lower end area of the separation region.

58. The control apparatus of claim 33, wherein the specification content analyzing means determines a processing pattern comprising maintaining the lower end portion of the pipette portion submerged in a reagent or a cleaning liquid to prevent generation of bubbles due to suction of air, wherein a liquid is drawn in and discharged at a high speed.

59. The control apparatus of claim 33, wherein the specification content analyzing means determines a processing pattern, wherein a percentage of a liquid drawn in from a container can be specified during agitation or cleaning.

60. The control apparatus of claim 33, wherein the processing pattern execution instruction means comprises sucking air.

61. The control apparatus of claim 33, wherein the processing pattern execution instruction means comprises maintaining a liquid suction speed and a discharge speed during reaction, agitation or cleaning faster than a liquid suction speed and a discharge speed during the magnetic particle separation process.

62. The control apparatus of claim 33, wherein the specification content analyzing means determines a processing pattern comprising:
   transferring a plurality of arrested magnetic particles to another position where a target substance bonded to the magnetic particles is subjected to processing,
   wherein the arrested magnetic particles adhere to the inner sidewall.

63. The control apparatus of claim 33, wherein the specification information is selected from the group consisting of material conditions, reaction conditions, and operation conditions.

64. The control apparatus of claim 63, wherein the material conditions are selected from the group consisting of materials kinds, quantities, accommodated positions and characteristics of a target substance, a sample, and magnetic particles; wherein the reaction conditions are selected from the group consisting of number of the reaction, incubation time, and temperature; and wherein the operation conditions include a specification of whether magnetic particles are attached to the inner sidewall by a magnetic field.

65. The control apparatus of claim 33, wherein the specification content analyzing means determines the processing pattern for one or more items that can be respectively processed successively using the same container cartridge, according to data set for each item; and wherein the data set includes a number of samples, a total process time, a time taken by each process contained in each item, and a container cartridge positions.

66. A control apparatus for controlling magnetic particles by a sample distributor, comprising:

a pipette tip comprising a front end portion having a diameter that is tapered off toward the front end, a reservoir portion with a greater diameter than the front end portion, a liquid passage narrower than the reservoir portion and larger than the front end portion to connect the front end portion and the reservoir portion, and a separation region in the liquid passage subjected to an action of a magnetic field;

a sample distributor unit comprising a nozzle removably fitted into an opening of the reservoir portion of the pipette tip, to apply a negative or positive pressure into the pipette tip to draw or discharge a liquid into or from the pipette tip;

a magnetic field source arranged so that it can be brought close to or away from an outside surface of the liquid passage;

a magnetic driving device for bringing the magnetic field source close to or away from the liquid passage; and a control device for controlling an operation and a movement of the sample distributor unit, an attaching and a detaching of the pipette tip to and from the nozzle, and a bringing of the magnetic field source close to or away from the pipette tip, according to a specification information which is entered into the control apparatus, the specification information including at least one operation condition for specifying:

whether the magnetic particles are attracted to an inner surface of the liquid passage by the magnetic field; and a selection from among: a specification of whether a suction and discharge operation is performed by the sample distributor, a position of the suction and discharge operation, a time of the suction and discharge operation, an order of the suction and discharge operation, a number of times of the suction and discharge operation, a quantity of the suction and discharge operation, and a speed of the suction and discharge operation.

* * * * *